United States Patent [19]

Takaya et al.

[11] Patent Number: 4,698,337
[45] Date of Patent: Oct. 6, 1987

[54] CEPHEM COMPOUNDS AND PROCESSES FOR PREPARATION THEREOF

[75] Inventors: Takao Takaya, Kawanishi; Hisashi Takasugi; Kiyoshi Tsuji; Toshiyuki Chiba, both of Osaka, all of Japan

[73] Assignee: Fujisawa Pharmaceutical Co., Ltd., Osaka, Japan

[21] Appl. No.: 912,212

[22] Filed: Sep. 25, 1986

Related U.S. Application Data

[60] Continuation of Ser. No. 715,400, Mar. 25, 1985, abandoned, which is a division of Ser. No. 91,961, Nov. 7, 1979, abandoned.

[30] Foreign Application Priority Data

Nov. 13, 1978 [GB] United Kingdom ............ 44226
Apr. 3, 1979 [GB] United Kingdom ............ 7911536
Jul. 3, 1979 [GB] United Kingdom ............ 7923193

[51] Int. Cl.⁴ .................. C07D 501/36; A61K 31/545
[52] U.S. Cl. .................... 514/206; 540/227; 540/228; 540/222
[58] Field of Search ............ 540/227; 514/206

[56] References Cited

U.S. PATENT DOCUMENTS 4,024,133 5/1977 Cook et al. .................... 540/228

FOREIGN PATENT DOCUMENTS 2714880 10/1978 Fed. Rep. of Germany ...... 540/228

Primary Examiner—Donald G. Daus
Assistant Examiner—William A. Teoli, Jr.
Attorney, Agent, or Firm—Oblon, Fisher, Spivak, McClelland & Maier

[57] ABSTRACT

The invention relates to novel cephem compounds, of high antimicrobial activity, of the formula

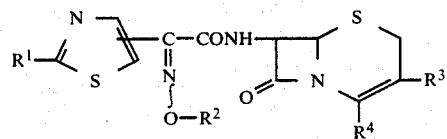

wherein
$R^1$ is amino or protected amino,
$R^2$ is lower alkyl substituted with 1 to 3 halogen atoms,
$R^3$ is thiadiazolylthiomethyl which may be substituted with lower alkyl, or tetrazolylthiomethyl which may be substituted with lower alkyl or lower alkenyl, and
$R^4$ is carboxy or protected carboxy, and a pharmaceutically acceptable salt thereof.

12 Claims, No Drawings

CEPHEM COMPOUNDS AND PROCESSES FOR PREPARATION THEREOF

This application is a continuation of application Ser. No. 715,400, filed Mar. 25, 1985, abandoned, which is a divisional of Ser. No. 06/091,961, filed Nov. 7, 1979, abandoned.

This invention relates to new cephem compounds. More particularly, it relates to new 3,7-disubstituted-3-cephem-4-carboxylic acid, its pharmaceutically acceptable salt, which have antimicrobial activities, and processes for preparation thereof, and to pharmaceutical composition comprising the same and methods of using the same prophylactically and therapeutically for treatment of infectious diseases in human being and animals.

Accordingly, the objects of this invention are to procide:

new 3,7-disubstituted-3-cephem-4-carboxylic acid, its pharmaceutically acceptable salt, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals.

The cephem compounds provided by this invention can be represented by the formula (I):

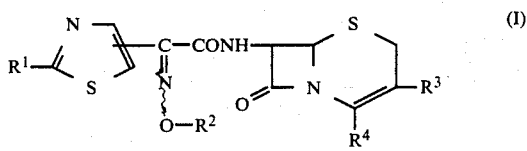

(I)

wherein
$R^1$ is amino or protected amino,
$R^2$ is lower alkyl substituted with 1 to 3 substituent(s) selected from the groups consisting of cyano, hydroxy, protected hydroxy, amino, lower alkoxycarbonylamino, azido, lower alkenylthio and halogen,
$R^3$ is lower alkyl, lower alkanoyloxymethyl, carbamoyloxymethyl or a heterocyclicthiomethyl which may be substituted with lower alkyl or lower alkenyl, and
$R^4$ is carboxy or protected carboxy, provided that when $R^2$ is alkyl substituted with cyano, $R^3$ is not lower alkanoyloxy-methyl,
and pharmaceutically acceptable salt thereof.

The compound (I) of this invention can be prepared by the processes as shown in the following scheme.

Process A: N—Acylation

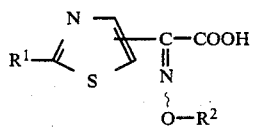

(III)
or its reactive derivative at the carboxy group or a salt thereof

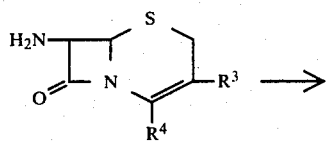

(II)
or its reactive derivative at the amino group or a salt thereof

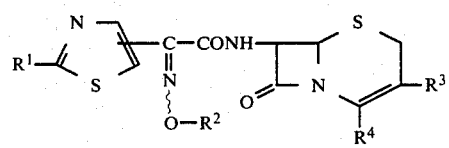

(I)
or its salt

Process B: Thioetherification

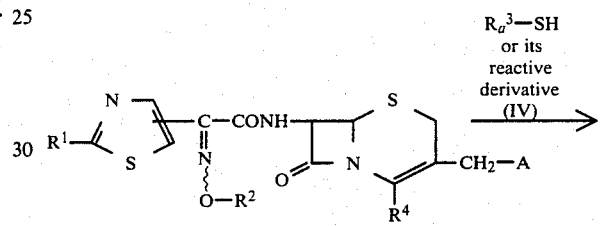

(Ia)
or its salt

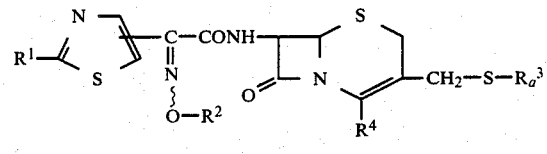

(Ib)
or its salt

Process C: Hydrogenation

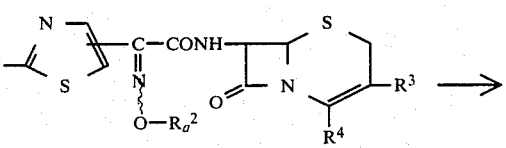

(Ic)
or its salt

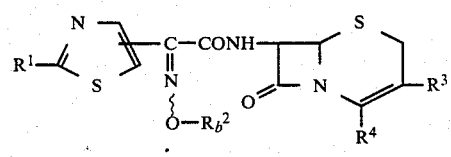

or its salt

Process D: Elimination of amino-protective group for $R_a^1$

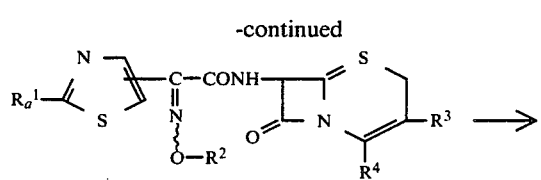

(I_c) or its salt

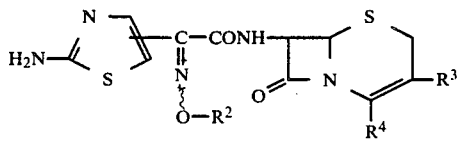

(I_f) or its salt

Process E: Elimination of hydroxy-protective group

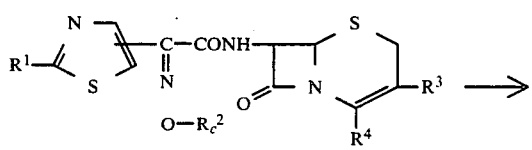

(I_g) or its salt

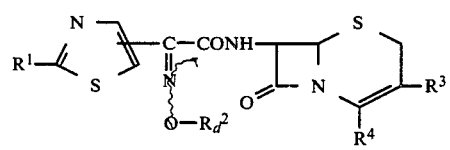

(I_h) or its salt

Process F: Carboxy formation

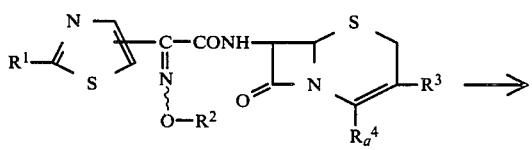

(I_i) or its salt

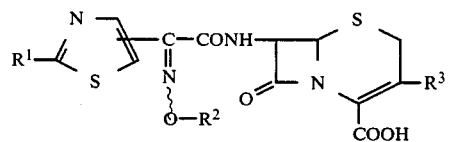

(I_j) or its salt

Process G: Elimination of amino protective group for $R_c^2$

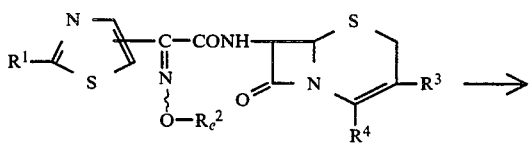

(I_k) or its salt

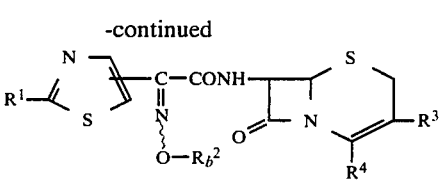

(I_d) or its salt wherein
$R^1$, $R^2$, $R^3$ and $R^4$ are each as defined above,
$R_a^1$ is protected amino,
$R_a^2$ is lower alkyl substituted with azido,
$R_b^2$ is lower alkyl substituted with amino,
$R_c^2$ is lower alkyl substituted with protected hydroxy,
$R_d^2$ is lower alkyl substituted with hydroxy,
$R_e^2$ is lower alkyl substituted with lower alkoxycarbonylamino,
$R_a^3$ is a heterocyclic which may be substituted with lower alkyl or lower alkenyl,
$R_a^4$ is protected carboxy, and
A is a group which can be substituted with a group: $R_a^3$—S— in which $R_a^3$ is as defined above.

Some of the starting compound (III) used in Process A are novel and can be represented by the following formula:

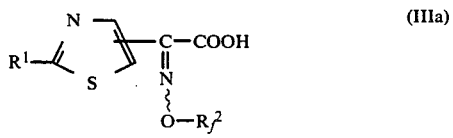

(IIIa)

wherein
$R^1$ is amino or protected amino, and
$R_f^2$ is lower alkyl substituted with a substituent selected from the groups consisting of hydroxy, protected hydroxy, amino, lower alkoxycarbonylamino, azido and lower alkenylthio,
and its ester and a salt thereof.

The stating compound (IIIa) can be prepared by the methods illustrated below.

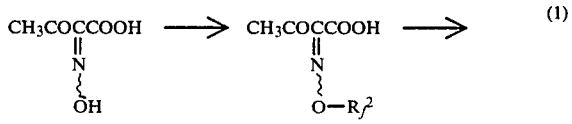

(1)

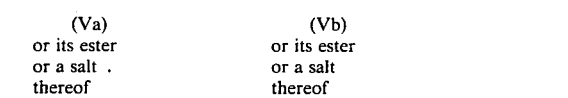

(Va) or its ester or a salt thereof (Vb) or its ester or a salt thereof

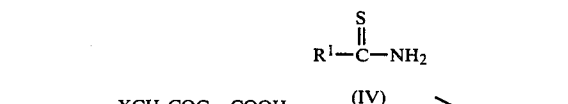

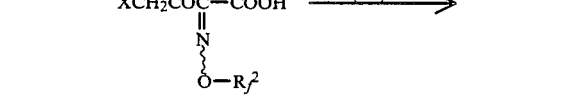

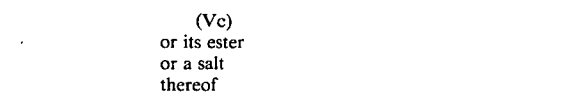

(Vc) or its ester or a salt thereof

-continued $$\text{(III'a) or its ester or a salt thereof}$$

$$\text{(Vd) or its ester or a salt thereof} \xrightarrow{R_f^2-ONH_2 \;(VI)\; \text{or its salt}} \text{(IIIa) or its ester or a salt thereof} \quad (2)$$

$$\text{(Ve) or its ester or a salt thereof} \longrightarrow \text{(IIIa) or its ester or a salt thereof} \quad (3)$$

$$\text{(Vf) or its ester or a salt thereof} \xrightarrow{R^{2'}-SH \;(VII)} \text{(IIIb) or its ester or a salt thereof} \quad (4)$$

$$\text{(IIIc) or its ester or a salt thereof} \longrightarrow \text{(IIId) or its ester or a salt thereof} \quad (5)$$

$$\text{(IIId) or its ester or a salt thereof} \longrightarrow \text{(IIIc) or its ester or a salt thereof} \quad (6)$$

$$\text{(IIIe) or its salt} \longrightarrow \text{(IIIf) or its salt} \quad (7)$$

$$\text{(IIIg) or its ester or a salt thereof} \longrightarrow \text{(IIIh) or its ester or a salt thereof} \quad (8)$$

$$R^1 \underset{S}{\overset{N}{\diagdown}} \overset{}{\underset{}{}} C-COOH \underset{\underset{O-R_c^2}{N}}{\overset{\|}{}} \longrightarrow \quad (9)$$

(IIIi)
or its ester or
a salt thereof $$R^1 \underset{S}{\overset{N}{\diagdown}} \overset{}{\underset{}{}} C-COOH \underset{\underset{O-R_d^2}{N}}{\overset{\|}{}}$$

(IIIj)
or its ester or
a salt thereof $$R^1 \underset{S}{\overset{N}{\diagdown}} \overset{}{\underset{}{}} C-COOH \underset{\underset{O-R_d^2}{N}}{\overset{\|}{}} \longrightarrow \quad (10)$$

(IIIj)
or its ester or
a salt thereof $$R^1 \underset{S}{\overset{N}{\diagdown}} \overset{}{\underset{}{}} C-COOH \underset{\underset{O-R_c^2}{N}}{\overset{\|}{}}$$

(IIIi)
or its ester or
a salt thereof wherein
$R^1$, $R_a^1$, $R_c^2$, $R_d^2$, $R_b^2$, and $R_f^2$ are each as defined above,
X is halogen,
$R_g^2$ is lower alkyl substituted with halogen,
$R^{2'}$ is lower alkenyl,
$R_h^2$ is lower alkyl substituted with lower alkenylthio,
$R_i^2$ is lower alkyl substituted with lower alkoxycarbonylamino, and
Z is esterified carboxy.

The terms and definitions described in this specification are illustrated as follows.

(a) Partial structure of the formula:

$$R^1 \underset{S}{\overset{N}{\diagdown}} \overset{}{\underset{}{}} C-CO- \underset{\underset{O-R^2}{N}}{\overset{\|}{}}$$

is intended to mean both of the geometric formula:

$$R^1 \underset{S}{\overset{N}{\diagdown}} \overset{}{\underset{N-O-R^2}{}} C-CO- \quad \text{and} \quad R^1 \underset{S}{\overset{N}{\diagdown}} \overset{}{\underset{R^2-O-N}{}} C-CO-$$

(S) (A)

The geometry of the formula (S) is referred to as "syn" and another formula (A) is referred to as "anti".

Accordingly, one isomer of the compound having the partial structure shown by the above formula (S) is referred to as "syn isomer" and another isomer of the compound having the alternative one shown by the above formula (A) is referred to as "anti isomer", respectively.

From the view point of structure-activity relationship, it is to be noted that a syn isomer of the compound (I) tends to be of much higher antimicrobial activity than the corresponding anti isomer, and accordingly the syn isomer of the compound (I) is more preferable antimicrobial agent than the corresponding anti isomer in the prophylactic and therapeutic value.

(b) The thiazolyl group of the formula:

$$R^1 \underset{S}{\overset{N}{\diagdown}}$$

(wherein $R^1$ is as defined above) is well known to lie in tautomeric relation with a thazolinyl group of the formula $$R^{1'} \underset{S}{\overset{HN}{\diagdown}}$$

(wherein $R^{1'}$ is imino or protected imino).

The tautomerism between the said thiazolyl and thiazolinyl groups can be illustrated by the following equilibrium:

$$R^1 \underset{S}{\overset{N}{\diagdown}} \rightleftarrows R^{1'} \underset{S}{\overset{HN}{\diagdown}}$$

(wherein $R^1$ and $R^{1'}$ are each as defined above).

Accordingly, it is to be understood that both of the said groups are substantially the same, and the tautomers consisting of such groups are regarded as the same compounds, especially in the manufacturing chemistry. Therefore, both of the tautomeric forms of the compounds having such groups in their molecule are included in the scope of this invention and designated inclusively with one expression "thiazolyl" and represented by the formyla:

$$R^1 \underset{S}{\overset{N}{\diagdown}}$$

(wherein $R^1$ is as defined above) only for the convenient sake throughout this specification.

In the above and subsequent descriptions of this specification, suitable examples and illustration of the various definitions which this invention intends to include within the scope thereof are explained in detail as follows.

The term lower is used to intend a group having 1 to 6 carbon atom(s), unless otherwise provided.

The term "protective group" in the "protected amino" may include a conventional N-protective group such as acyl, substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, or the like.

Suitable acyl for the N-protective group may be aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s);

lower alkoxycarbonyl having 2 to 7 carbon atoms (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 2 to 6 carbon atoms;

lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, naphthoyl, phthaloyl, indancarbonyl, etc.);

ar(lower)alkanoyl (e.g. phenylacetyl, phenylpropionyl, etc.);

ar(lower)alkoxycarbonyl (e.g. benzyloxycarbonyl, phenethyloxycarbonyl, etc.); and the like.

The acyl as stated above may have 1 to 3 suitable substituent(s) such as halogen (e.g. chlorine, bromine, iodine or fluorine), hydroxy, cyano, nitro, lower alkoxy (e.g. methoxy, ethoxy, propoxy, isopropoxy, etc.), lower alkyl (e.g. methyl, ethyl, propyl, isopropyl, butyl, etc.), lower alkenyl (e.g. vinyl, allyl, etc.), aryl (e.g. phenyl, tolyl, etc.), or the like, and preferable example is mono(or di or tri)halo(lower)alkanoyl (e.g. chloroacetyl, dichloroacetyl, trifluoroacetyl, etc.).

And further, the reaction product of a silan, boron, aluminium or phosphorus compound with the amino group may also be included in the N-protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

The term "lower alkyl" may include a residue of straight and branched alkane having 1 to 6 carbon atom(s) such as methyl, ethyl, propyl, isopropyl, butyl, isobutyl, t-butyl, pentyl, neopentyl, hexyl and the like, and preferably the one having 1 to 4 carbon atom(s).

The term "protective group" in the "protected hydroxy" may include a conventional O-protective group such as acyl as aforementioned, or the like.

The term "lower alkoxycarbonylamino" may include methoxycarbonylamino, ethoxycarbonylamino, propoxycarbonylamino, iso-propoxycarbonylamino, butoxycarbonylamino, tert-butoxycarbonylamino, pentyloxycarbonylamino, hexyloxycarbonylamino, and the like.

The term "lower alkenylthio" may include straight and branched alkenylthio having 2 to 6 carbon atoms, such as vinylthio, allylthio, 1-butenylthio, 2-pentenylthio, 4-pentenylthio, 5-hexenylthio and the like, and preferably the one having 2 to 4 carbon atoms.

The term "halogen" may include bromine, chlorine, fluorine or iodine, and preferably bromine, chlorine or fluorine.

The term "lower alkanoyloxymethyl" may include formyloxymethyl, acetoxymethyl, propionyloxymethyl, butyryloxymethyl, isobutyryloxymethyl, valeryloxymethyl, isovaleryloxymethyl, pivaloyloxymethyl, and the like, and preferably the one having 1 to 4 carbon atoms.

The terms "heterocyclic" and "heterocyclic moiety" of the "heterocyclicthiomethyl" means saturated or unsaturated, monocyclic or polycyclic heterocyclic group containing at least one hetero-atom such as oxygen, sulfur, nitrogen and the like.

And, preferable heterocyclic group may be unsaturated 3 to 8-membered, preferably 5 to 6 membered heteromonocyclic group containing 1 to 4 nitrogen atoms, for example, pyrrolyl, pyrrolinyl, imidazolyl, pyrazolyl, pyridyl and its N-oxide, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered, preferably 5 to 6-membered heteromonocyclic group containing 1 to 4 nitrogen atoms, for example, pyrrolidinyl, imidazolidinyl, piperidino, piperazinyl, etc.;

unsaturated condensed heterocyclic group containing 1 to 4 nitrogen atoms, for example, indolyl, isoindolyl, indolizinyl, benzimidazolyl, quinolyl, isoquinolyl, indazolyl, benzotriazolyl, etc.; unsaturated 3 to 8-membered, preferably 5 to 6-membered heteromonocyclic group containing 1 to 2 oxygen atoms and 1 to 3 nitrogen atoms, for example, oxazolyl, isoxazolyl, oxadiazolyl (e.g. 1,2,4-oxadiazolyl, 1,3,4-oxadiazolyl, 1,2,5-oxadiazolyl, etc.) etc.; saturated 3 to 8-membered, preferably 5 to 6-membered heteromonocyclic group containing 1 to 2 oxygen atoms and 1 to 3 nitrogen atoms, for example, morpholinyl, etc.;

unsaturated condensed heterocyclic group containing 1 to 2 oxygen atoms and 1 to 3 nitrogen atoms, for example, benzoxazolyl, benzoxadiazolyl, etc.; unsaturated 3 to 8-membered, preferably 5 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.;

saturated 3 to 8-membered, preferably 5 to 6-membered heteromonocyclic group containing 1 to 2 sulfur atoms and 1 to 3 nitrogen atoms, for example, thiazolidinyl, etc.;

unsaturated 3 to 8-membered, preferably 5 to 6 membered heteromonocyclic group containing a sulfur atom, for example, thienyl, etc.;

unsaturated condensed heterocyclic group containing 1 to 2 sulfur atoms and 1 to 3 nitrogen atoms, for example, benzothiazolyl, benzothiadiazolyl, etc. and the like;

wherein said heterocyclic group may have 1 to 2 substituents selected from lower alkyl (e.g. methyl, ethyl, propyl, isopropyl, butyl, isobutyl, pentyl, cyclopentyl, hexyl, cyclohexyl, etc.) and lower alkenyl (e.g. vinyl, allyl, butenyl, etc.):

The term "protected carboxy" may include esterified carboxy, amidated carboxy or the like.

Suitable examples of "the ester" and "ester moiety" in the "esterified carboxy" may be lower alkyl ester (e.g. methyl ester, ethyl ester, propyl ester, isopropyl ester, butyl ester, isobutyl, ester, t-butyl ester, pentyl ester, t-pentyl ester, hexyl ester, 1-cyclopropylethyl ester, etc.);

lower alkenyl ester (e.g. vinyl ester, allyl ester, etc.);

lower alkynyl ester (e.g. ethynyl ester, propynyl ester, etc.);

lower alkoxy(lower)alkyl ester (e.g. methoxymethyl ester, ethoxymethyl ester, isopropoxymethyl ester, 1-methoxyethyl ester, 1-ethoxyethyl ester, etc.);

lower alkylthio(lower)alkyl ester (e.g. methylthiomethyl ester, ethylthiomethyl ester, ethylthioethyl ester, isopropylthiomethyl ester, etc.);

halo(lower)alkyl ester (e.g. 2-iodoethyl ester, 2,2,2-trichloroethyl ester, etc.);

lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g. mesylmethyl ester, 2-mesylethyl ester, etc.);

ar(lower)alkyl, for example, phenyl(lower)alkyl ester which may have one or more suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) (e.g. phenyl ester, tolyl ester, t-butylphenyl ester, xylyl ester, mesityl ester, cumenyl ester, salicyl ester, etc.);

an ester with a silyl compound such as tri(lower)alkylsilyl compound, di(lower)alkylalkoxysilyl compound or tri(lower)alkoxysilyl compound, for example, tri(lower)alkylsilyl ester (e.g. trimethyl silyl ester, triethylsilyl ester, etc.);

di(lower)alkylalkoxy silyl ester (e.g. dimethylmethoxysilyl ester, dimethylethoxysilyl ester, diethylmethoxysilyl ester, etc.) or tri(lower)alkoxysilyl ester (e.g. trimethoxysilyl ester, triethoxysilyl ester, etc.), or the like.

The term "a group which can be substituted with a group: $R_a^3$ —S—" may include an acid residue such as lower alkanoyloxy (e.g. acetoxy, propionyloxy, etc.), halogen as aforementioned and the like.

More particularly, the preferable example for $R^1$ may be amino or acylamino[more preferably, lower alkanoylamino (e.g. formamido, acetamido, etc.)].

The preferable example for $R^2$ may be illustrated as follows:

cyano(lower)alkyl (e.g. cyanomethyl, cyanoethyl, cyanopropyl, cyanobutyl, cyanopentyl, etc.);

hydroxy(lower)alkyl (e.g. hydroxymethyl, hydroxyethyl, hydroxypropyl, hydroxybutyl, hydroxypentyl, etc.);

protected hydroxy(lower)alkyl such as lower alkanoyloxy(lower)alkyl (e.g. formyloxymethyl, acetoxymethyl, formyloxyethyl, acetoxyethyl, formyloxypropyl, formyloxybutyl, etc.); benzoyloxy(lower)alkyl (e.g. benzoyloxymethyl, benzoyloxyethyl, benzoyloxypropyl, benzoyloxybutyl, etc.) and the like;

amino(lower)alkyl (e.g. aminomethyl, aminoethyl, aminopropyl, aminobutyl, aminopentyl, etc.);

lower alkoxycarbonylamino(lower)alkyl (e.g. methoxycarbonylaminomethyl, ethoxycarbonylaminoethyl, propoxycarbonylaminomethyl, butoxycarbonylaminoethyl, t-butoxycarbonylaminomethyl, t-butoxycarbonylaminoethyl, t-butoxycarbonylaminopropyl, t-butoxycarbonylaminobutyl, t-butoxycarbonylaminopentyl, t-butoxycarbonylaminohexyl, etc.);

azido(lower)alkyl (e.g. azidomethyl, azidoethyl, azidopropyl, azidobutyl, etc.);

lower alkenylthio(lower)alkyl (e.g. vinylthiomethyl, alkylthiomethyl, 1-propenylthiomethyl, vinylthioethyl, allylthioethyl, 1-propenylthioethyl, butenylthioethyl, pentenylthiopropyl, hexenylthiopentyl, etc.); and mono(or di or tri)halo(lower)alkyl (e.g. bromomethyl, bromoethyl, bromopropyl, bromobutyl, chloromethyl, chloroethyl, chloropropyl, chlorobutyl, fluoromethyl, fluoroethyl, trifluoroethyl, fluoropropyl, fluorobutyl, etc.).

The preferably examples for $R^3$ may be methyl;

acetoxymethyl;

carbamoyloxymethyl;

thiadiazolylthiomethyl (e.g. 1,3,4-thiadiazol-2-ylthiomethyl, etc.) which may be substituted with lower alkyl (e.g. methyl, ethyl, propyl, etc.);

triazolylthiomethyl (e.g. 1H-1,2,3-triazol-5-ylthiomethyl, etc.) which may be substituted with lower alkyl (e.g. methyl, ethyl, propyl, etc.); and tetrazolylthiomethyl (e.g. 1H-tetrazol-5-ylthiomethyl, etc.) which may be substituted with lower alkyl (e.g. methyl, ethyl, propyl, butyl, pentyl, hexyl, etc.) or lower alkenyl (e.g. vinyl, allyl, etc.).

The preferably example for $R^4$ may be carboxy.

With regard to the terms "protected amino", "protected hydroxy" and "protected carboxy", it is to be understood that these groups bear the meaning not only in synthetic manufacture of the object compound by chemical process(es), but also in physiological and pharmaceutical properties of the object compound per se.

That is, in the meaning of the synthetic manufacture, free amino group, free hydroxy group and/or free carboxy group may be transformed into the "protected amino", "protected hydroxy" and/or "protected carboxy" as mentioned above before conducting the process(es) for preventing any possible undesired side reaction(s), and the "protected amino", "protected hydroxy" and/or "protected carboxy" group in the resultant compound may be transformed into free amino, hydroxy and/or carboxy group after the reaction is conducted. This will be apparent from the explanation of the processes in the following.

On the other hand, in the meaning of the physiological and pharmaceutical properties of the object compound, the compound bearing the "protected amino", "protected hydroxy" and/or "protected carboxy" group is optionally used for improving the properties such as solubility, stability, absorbability, toxicity of the particularly active object compound bearing the free amino, hydroxy and/or carboxy group.

Suitable "pharmaceutically acceptable salt" of the object compound (I) may be conventional nontoxic salt, and may include a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like.

The processes for preparing the object compounds (I) of the present invention are explained in details in the following.

Process A: N-Acylation

A compound (I) or its salt can be prepared by reacting a 7-amino-3-cephem compound (II) or its reactive derivative at the amino group or a salt thereof with a carboxylic acid (III) or its reactive derivative at the carboxy group or a salt thereof according to a conventional manner of so-called amidation reaction well known in β-lactam chemistry.

The starting compound (III) includes both of known and new ones, and the new compound (III) can be prepared according to the methods as explained in this specification.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with a ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.), and the like.

Suitable salt of the compound (II) may be referred to the one as exemplified for the compound (I).

Suitable reactive derivative at the carboxy group of the compound (II) may include, for example, an acid halide, an acid anhydride, an activated amide, an activated ester, and the like, and preferably acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivatives of the compounds (II) and (III) can be optionally selected from the above according to the kind of the compounds (II) and (III) to be used practically, and to the reaction conditions.

Suitable salt of the compound (III) may include a salt with an inorganic base such as alkali metal salt (e.g. sodium salt, potassium salt, etc.) and an alkaline earth metal salt (e.g. calcium salt, magnesium salt, etc.), a salt with an organic base such as tertiary amine (e.g. trimethylamine salt, triethylamine salt, N,N-dimethylaniline salt, pyridine salt, etc.), a salt with an inorganic acid (e.g. hydrochloride, hydrobromide, etc.) and the like.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction, or an optional mixture thereof.

When the acylating agent (III) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphoryl chloride, phosgene or the like.

In order to obtain a syn isomer of the compound (I) selectively and in high yield, it is preferable to use a syn-isomer of the acylating agent (III), and to conduct the reaction under a selected reaction condition, for example, in the presence of a Vilsmeier reagent as mentioned above and under around neutral condition.

The reaction temperature is not critical and the reaction can be usually carried out under cooling to warming.

The object compound (I) and its salt are useful as an antimicrobial agent, and a part thereof can be also used as a starting material in the following processes.

Process B: Thioetherification

The object compound ($I_b$) or its salt can be prepared by reacting a compound ($I_a$) or its salt with a compound (IV) or its reactive derivative at the mercapto group.

Suitable salt of the compound ($I_a$) can be referred to the ones exemplified for the compound (I).

The suitable reactive derivative at the mercapto group of the compound (IV) may include a metal salt such as alkali metal salt (e.g. sodium salt, potassium salt, etc) or the like.

This reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, or any other solvent which does not adversely effect the reaction, preferably in ones having strong polarities. Among the solvents, hydrophilic solvents may be used in a mixture with water. The reaction is preferably carried out in weekly basic or around neutral condition. When the compound ($I_a$) and/or the thiol compound (IV) is used in a free form, the reaction is preferably conducted in the presence of a base, for example, inorganic base such as alkali metal hydroxide, alkali metal carbonate, alkali metal bicarbonate, organic base such as trialkylamine, pyridine, and the like. The reaction temperature is not critical, and the reaction is usually carried out at ambient temperature or under warming. The reaction product can be isolated from the reaction mixture by a conventional method.

The reaction of the compound ($I_a$) with the compound (IV) includes, within its scope, the cases that the protected carboxy group or salt of the compound ($I_a$) may be converted into free carboxy group; that the protected amino group may be converted into free amino group; and that the protected hydroxy group may be converted into hydroxy group; respectively in the course of the reaction or in post-treatment.

Process C: Hydrogenation

A compound ($I_d$) or its salt can be prepared by hydrogenating a compound ($I_c$) or its salt.

The hydrogenation reaction may be conducted in accordance with a conventional method which is able to convert an azido group to an amino group without conversion of the oxime moiety. Such hydrogenation may include catalytic reduction using a catalyst (e.g. palladium carbon, palladium black, platinum, colloidal platinum, Raney nickel, etc.), chemical reduction using sodium borohydride etc., and the like. The reaction can be conducted in a solvent such as water, methanol, ethanol, acetic acid and the other solvent which does not adversely effect the reaction. The reaction temperature is not critical and the reaction can be usually carried out at ambient temperature to under warming.

Process D: Elimination of amino-protective group for $R_a^1$

A compound ($I_f$) or its salt can be prepared by subjecting a compound ($I_e$) or its salt to elimination reaction of the protective group in the protected amino group for $R_a^1$.

The elimination reaction may be conducted in accordance with a conventional method such as hydrolysis, reduction or the like. These methods may be selected according to the kind of the protective group to be eliminated.

The hydrolysis may include a method using an acid (acidic hydrolysis), a base (basic hydrolysis) or hydrazine, and the like.

Among these methods, hydrolysis using an acid is one of the common and preferable methods for eliminating the protective group such as an acyl group, for example, substituted or unsubstituted lower alkanoyl, substituted or unsubstituted lower alkoxycarbonyl, substituted or unsubstituted ar(lower)alkoxycarbonyl, lower cycloalkoxycarbonyl, substituted phenylthio, substituted alkylidene, substituted aralkylidene, substituted cycloalkylidene or the like.

Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the protective group to be eliminated. The acidic hydrolysis can be conducted in the presence or absence of a solvent.

Suitable solvent may be a conventional organic solvent, water or a mixture thereof, which does not adversely influence this reaction. Particularly, when the hydrolysis is conducted with trifluoroacetic acid, the reaction may be accelerated by addition of anisole.

The hydrolysis using a base can be preferably applied for eliminating the protective group such an an acyl group, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-7-undecane, anionexchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl, for example, halo(lower)alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, etc.), 2-pyridylmethoxycarbonyl, etc., arlkyl (e.g. benzyl, benzhydryl, trityl, etc.) and the like.

Suitable reduction may include, for example, reduction using an alkali metal borohydride (e.g. sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

The reaction temperature is not critical and may be optionally selected in consideration of the chemical property of the starting compound and reaction product as well as the kind of the N-protective group and the method to be applied, and the reaction is preferably carried out under a mild condition such as under cooling, at ambient temperature or slightly elevated temperature.

This process includes in its scope the cases that the protected hydroxy for $R^2$ and/or the protected carboxy for $R^4$ is simultaneously transformed into the free hydroxy and/or carboxy group in the course of the above reaction or in the post-treatment.

As to this process, it is to be understood that the purpose of this process lies in providing the generally more active compound $(I_f)$ by eliminating the protective group in the protected amino group for $R_a^1$ of the compound $(I_e)$ prepared by the other processes as mentioned above or below.

Process E: Elimination of hydroxy-protective group

A compound $(I_h)$ or its salt can be prepared by subjecting a compound $(I_g)$ or its salt to elimination reaction of the protective group in the protected hydroxy group for $R_c^2$.

The elimination reaction may be conducted in accordance with a conventional method such as hydrolysis, reduction or the like, and the suitable examples explained in the Process D are applicable in this Process E.

This process also includes in its scope the cases that the protected amino for $R^1$ and/or protected carboxy for $R^4$ is simultaneously transformed into the free amino and/or carboxy group in the course of the above reaction or the post-treatment.

Process F: Carboxy formation

The compound $(I_j)$ or its salt can be prepared by transforming the protected carboxy of the compound $(I_i)$ or its salt, into a free carboxy.

This process is to provide a free carboxy compound $(I_j)$ or its salt, which generally exhibits higher antimicrobial activities as compared with the corresponding protected carboxy compound $(I_i)$ or its salt.

The method to be applied to this process includes conventional ones such as hydrolysis, reduction and the like.

The method of hydrolysis includes a conventional one using an acid, base, enzyme or enzymatic preparation, and the like.

Suitable example of the acid and base are to be referred to those as exemplified in the above Process D, and the acidic or basic hydrolysis can be carried out in a similar manner to that of the Process D.

Suitable enzyme includes an esterase and esterase preparation which exhibits an esterase activity such as a cultured broth of microorganism or processed materials of microorganism, the preparation of animal or plant tissues, or the like, and preferably a cultured broth of microorganism or processed material thereof.

The method of the reduction for this process may be carried out in a similar manner to that of the above Process D.

This process includes within its scope the cases that the protective group in the protected amino for $R^1$ and/or in the protected hydroxy-substituted alkyl for $R^2$ is eliminated in the course of the reaction or the post-treatment.

Process G: Elimination of amino-protective group for $R_e^2$

The compound $(I_d)$ or its salt can be prepared by subjecting the compound $(I_k)$ or its salt to elimination reaction of the amino-protective group for $R_e^2$.

The present reaction can be carried out in substantially the same manner as that of Process D. Accordingly, the detailed explanations described in Process D can be referred to the present reaction.

The compound obtained in accordance with the processes as explained above can be isolated and purified in a conventional manner.

In case that the object compound (I) has free carboxy and/or free amino group in the molecule, it may be transformed into its pharmaceutically acceptable salt by a conventional method.

The object compound (I) and its pharmaceutically acceptable salt exhibit high antimicrobial activities inhibiting the growth of a wide variety of pathogenic microorganisms including Gram-positive and Gram-negative bacteria and are useful as antimicrobial agents.

The following compounds can be prepared according to the aforementioned processes.

(1) 7-[2-(2-aminothiazol-4-yl)-2-cyanomethoxyiminoacetamido]cephalosporanic acid (syn isomer)

(2) 7-[2-(2-aminothiazol-4-yl)-2-cyanomethoxyiminoacetamido]-3-(1-methyl-1H-tetrazol-5-yl)thiomethyl-3-cephem-4-carboxylic acid (syn isomer).

(3) 7-[2-(2-aminothiazol-4-yl)-2-cyanomethoxyiminoacetamido]-3-(1,3,4-thiadiazol-2-yl)thiomethyl-3-cephem-4-carboxylic acid (syn isomer)

(4) 7-[2-(2-aminothiazol-4-yl)-2-cyanomethoxyiminoacetamido]-3-(1-allyl-1H-tetrazol-5-yl)thiomethyl-3-cephem-4-carboxylic acid (syn isomer)

(5) 7-[2-(2-aminothiazol-4-yl)-2-cyanomethoxyiminoacetamido]-3-(1-n-hexyl-1H-tetrazol-5-yl)thiomethyl-3-cephem-4-carboxylic acid (syn isomer)

(6) 7-[2-(2-aminothiazol-4-yl)-2-(2-hydroxyethoxyimino)-acetamido]cephalosporanic acid (syn isomer)

(7) 7-[2-(2-aminothiazol-4-yl)-2-(2-hydroxyethoxyimino)acetamido]-3-methyl-3-cephem-4-carboxylic acid (syn isomer)

(8) 7-[2-(2-aminothiazol-4-yl)-2-(2-hydroxyethoxyimino)acetamido]-3-carbamoyloxymethyl-3-cephem-4-carboxylic acid (syn isomer)

(9) 7-[2-(2-aminothiazol-4-yl)-2-(2-hydroxyethoxyimino)acetamido]-3-(1-methyl-1H-tetrazol-5-yl)thiomethyl-3-cephem-4-carboxylic acid (syn isomer)

(10) 7-[2-(2-aminothiazol-4-yl)-2-(2-hydroxyethoxyimino)acetamido]-3-(1,3,4-thiadiazol-2-yl)thiomethyl-3-cephem-4-carboxylic acid (syn isomer)

(11) 7-[2-(2-aminothiazol-4-yl)-2-(2-hydroxyethoxyimino)acetamido]-3-(1-allyl-1H-tetrazol-5-yl)thiomethyl-3-cephem-4-carboxylic acid (syn isomer)

(12) 7-[2-(2-aminothiazol-4-yl)-2-(2-aminoethoxyimino)acetamido]-3-(1-methyl-1H-tetrazol-5-yl)thiomethyl-3-cephem-4-carboxylic acid (syn isomer)

(13) 7-[2-(2-aminothiazol-4-yl)-2-(2-azidoethoxyimino)acetamido]-3-(1,3,4-thiadiazol-2-yl)thiomethyl-3-cephem-4-carboxylic acid (syn isomer)

(14) 7-[2(2-aminothiazol-4-yl)-2-(2-bromoethoxyimino)acetamido]-3-(1,3,4-thiadiazol-2-yl)thiomethyl-3-cephem-4-carboxylic acid (syn isomer)

(15) 7-[2-(2-aminothiazol-4-yl)-2-(2,2,2-trifluoroethoxyimino)acetamido]cephalosporanic acid (syn isomer)

(16) 7-[2-(2-aminothiazol-4-yl)-2-(2,2,2-trifluoroethoxyimino)acetamido]-3-(1-methyl-1H-tetrazol-5-yl)thiomethyl-3-cephem-4-carboxylic acid (syn isomer)

(17) 7-[2-(2-aminothiazol-4-yl)-2-(2,2,2-trifluoroethoxyimino)acetamido]-3-(1,3,4-thiadiazol-2-yl)thiomethyl-3-cephem-4-carboxylic acid (syn isomer)

(18) 7-[2-(2-aminothiazol-4-yl)-2-(2,2,2-trifluoroethoxyimino)acetamido]-3-(1-allyl-1H-tetrazol-5-yl)thiomethyl-3-cephem-4-carboxylic acid (syn isomer)

(19) 7-[2-(2-aminothiazol-4-yl)-2-(2-chloroethoxyimino)acetamido]cephalosporanic acid (syn isomer)
(20) 7-[2-(2-aminothiazol-4-yl)-2-(2-aminopropoxyimino)acetamido]-3-(1-methyl-1H-tetrazol-5-yl)thiomethyl-3-cephem-4-carboxylic acid (syn isomer)
(21) 7-[2-(2-aminothiazol-4-yl)-2-(2-aminoethoxyimino)acetamido]-3-carbamoyloxymethyl-3-cephem-4-carboxylic acid (syn isomer)
(22) 7-[2-(2-aminothiazol-4-yl)-2-(2-aminoethoxyimino)acetamido]-3-methyl-3-cephem-4-carboxylic acid (syn isomer)
(23) 7-[2-(2-aminothiazol-4-yl)-2-(3-aminopropoxyimino)acetamido]-3-(1-allyl-1H-tetrazol-5-yl)thiomethyl-3-cephem-4-carboxylic acid (syn isomer)
(24) 7-[2-(2-aminothiazol-4-yl)-2-(2-chloroethoxyimino)acetamido]-3-(1-allyl-1H-tetrazol-5-yl)thiomethyl-3-cephem-4-carboxylic acid (syn isomer)
(25) 7-[2-(2-aminothiazol-4-yl)-2-(2-aminoethoxyimino)acetamido]-3-(1,3,4-thiadiazol-2-yl)thiomethyl-3-cephem-4-carboxylic acid (syn isomer)
(26) 7-[2-(2-aminothiazol-4-yl)-2-(2-aminoethoxyimino)acetamido]-3-(1-allyl-1H-tetrazol-5-yl)thiomethyl-3-cephem-4-carboxylic acid (syn isomer)
(27) 7-[2-(2-aminothiazol-4-yl)-2-(2-chloroethoxyimino)acetamido]-3-(1,3,4-thiadiazol-2-yl)thiomethyl-3-cephem-4-carboxylic acid (syn isomer)
(28) 7-[2-(2-aminothiazol-4-yl)-2-(2-aminoethoxyimino)acetamido]-3-(1H-1,2,3-triazol-5-yl)thiomethyl-3-cephem-4-carboxylic acid (syn isomer)

In order to show the utility of the object compound (I), the test data of some representative compounds (I) are shown in the following:

1. In vitro antibacterial activity:
(1) Test method:
In vitro antibacterial activity was determined by the two-fold agar-plate dilution method as described below.
One loopful of the 100-fold dilution of an overnight culture of each test strain in Trypticase-soy broth was streaked on heart infusion agar (HI-agar) containing graded concentration of the test compound and incubated at 37° C. for 20 hours. The minimal inhibitory concentration (MIC) was expressed in μg/ml.

(2) Test compounds:
No. 1: 7-[2-(2-aminothiazol-4-yl)-2-(2-cyanomethoxyimino)acetamido]-3-(1,3,4-thiadiazol-2-yl)thiomethyl-3-cephem-4-carboxylic acid (syn isomer)
No. 2: 7-[2-(2-aminothiazol-4-yl)-2-(2-hydroxyethoxyimino)acetamido]-3-(1-methyl-1H-tetrazol-5-yl)thiomethyl-3-cephem-4-carboxylic acid (syn isomer)
No. 3: 7-[2-(2-aminothiazol-4-yl)-2-(2-hydroxyethoxyimino)acetamido]-3-(1-allyl-1H-tetrazol-5-yl)thiomethyl-3-cephem-4-carboxylic acid hydrochloride (syn isomer)
No. 4: sodium 7-[2-(2-aminothiazol-4-yl)-2-(2-chloroethoxyimino)acetamido]cephalosporanate (syn isomer)
No. 5: 7-[2-(2-aminothiazol-4-yl)-2-(2,2,2-trifluoroethoxyimino)acetamido]-3 -(1-allyl-1H-tetrazol-5-yl)thiomethyl-3-cephem-4-carboxylic acid (syn isomer)
No. 6: 7-[2-(2-aminothiazol-4-yl)-2-(2-aminoethoxyimino)acetamido]-3-carbamoyloxymethyl-3-cephem-4-carboxylic acid (syn isomer)
No. 7: 7-[2-(2-aminothiazol-4-yl)-2-(2-aminoethoxyimino)acetamido]-3-(1,3,4-thiadiazol-2-yl)thiomethyl-3-cephem-4-carboxylic acid (syn isomer)
No. 8: 7-[2-(2-aminothiazol-4-yl)-2-(2-aminoethoxyimino)acetamido]-3-(1-allyl-1H-tetrazol-5-yl)yl)thiomethyl-3-cephem-4-carboxylic acid (syn isomer)
No. 9: 7-[2-(2-aminothiazol-4-yl)-2-(2-chloroethoxyimino)acetamido]-3-(1,3,4-thiadiazol-2-yl)thiomethyl-3-cephem-4-carboxylic acid (syn isomer)

| Test Strain | Compound | | | | | | | | |
|---|---|---|---|---|---|---|---|---|---|
| | 1 | 2 | 3 | 4 | 5 | 6 | 7 | 8 | 9 |
| Staphylococcus aureus 209 PJC-1 | 1.56 | 3.13 | 3.13 | 1.56 | 0.78 | 12.5 | 3.13 | 3.13 | 0.39 |
| Excherichia coli NIHJ JC-2 | 0.2 | 0.1 | 0.1 | 0.2 | 0.78 | 0.20 | 0.05 | 0.39 | 0.20 |
| Proteus vulgaris IAM-1025 | 0.025 | 0.025 | 0.025 | 0.025 | 0.025 | 0.20 | 0.10 | 0.20 | 0.025 |
| Klebsiella pneumoniae 20 | 0.025 | 0.025 | 0.05 | 0.025 | 0.05 | 0.10 | 0.025 | 0.025 | 0.025 |
| Proteus mirabilis 18 | 0.1 | 0.1 | 0.39 | 0.2 | 1.56 | 0.10 | 0.20 | 1.56 | 0.39 |
| Pseudomonus aeruginosa NCTC-10490 | 1.56 | 1.56 | 3.13 | 1.56 | 1.56 | 50 | 6.25 | 6.25 | 1.56 |

The process for preparing the starting compounds (IIIa) are explained in details in the following.

Process 1: Etherification

The compound (Vb) or its ester or a salt thereof, or the compound (IIIa) or its ester or a salt thereof can be prepared by reacting the compound (Va) or its ester or a salt thereof, or the compound (Ve) or its ester or a salt thereof with an etherifying agent, respectively.

The etherifying agent may include a compound of the formula:

$R_f^2$—X wherein
$R_f^2$ is as defined above, and
X is halogen.

The reaction is usually carried out in a solvent such as water, acetone, ethanol, diethyl ether, dimethylformamide or any other solvent which does not adversely influence the reaction, within a temperature range of cooling to heating, preferably in the presence of a base such as an inorganic or organic base as aforementioned in Process D as illustrated before.

Process 2: Halogenation

The compound (Vc) or its ester or a salt thereof can be prepared by reacting the compound (Vb) or its ester or a salt thereof with a halogenating agent.

The suitable halogenating agent may be halogen (e.g. bramine, chlorine, etc.), sulfuryl halide (e.g. sulfuryl bromide sulfuryl chloride, etc.), N-halosuccinimide (e.g. N-bromosuccinimide, etc.) or the like.

The reaction is usually carried out in a solvent such as acetone, diethyl ether, N,N-dimethylformamide, tetrahydrofuran, ethyl acetate, acetic acid or any other solvent which does not adversely influence the reaction. The reaction temperature is not critical and the reaction may be preferably conducted within a temperature range of cooling to somewhat elevated temperature.

Process 3: Thiazole ring formation

The compound (IIIa') or its ester or a salt thereof can be prepared by reacting the compound (Vc) or its ester or a salt thereof with a thiourea compound (IV).

The reaction is usually conducted in a solvent such as water, alcohol (e.g. methanol, ethanol, etc.), benzene, acetone, N,N-dimethylformamide, tetrahydrofuran, diethyl ether, dioxane or any other solvent which does not adversely influence the reaction.

The reaction temperature is not critical and the reaction may be preferably carried out within a temperature range of ambient temperature to heating.

Process 4: Oximation

The compound (IIIa) or its ester or a salt thereof can be prepared by reacting a compound (Vd) or its ester or a salt thereof with a hydroxyamine derivative of the formula (VI) or its salt. Suitable salt of the hydroxyamine derivative (VI) may be hydrochloride, hydrobromide, sulfate or the like.

The reaction is usually conducted in a conventional solvent such as water, alcohol, tetrahydrofuran, acetonitrile, dimethylsulfoxide, pyridine or any other solvent which does not adversely influence the reaction, or a mixture thereof, and the reaction temperature is not critical, and the reaction is preferably carried out under a mild condition, for example, under cooling to ambient temperature.

In case that a salt of the hydroxyamine derivative (VI) is used as a reagent, the reaction is preferably conducted in the presence of a conventional base as aforementioned in Process D.

Process 5:

The compound (IIIb) or its ester or a salt thereof can be prepared by reacting the compound (Vf) or its ester or a salt thereof with lower alkenylmercaptan (VII) such as allylmercaptan, 3-butenylmercaptan, 4-pentenylmercaptan, and the like.

The reaction is usually conducted in a conventional solvent such as water, alcohol, tetrahydrofuran, acetonitrile, dimethylformamide, pyridine, or any other solvent which does not adversely influence the reaction, or a mixture thereof. The reaction temperature is not critical, and the reaction may be preferably carried out under a mild condition such as under cooling or at ambient temperature.

The reaction can be conducted preferably in the presence of a conventional base as aforementioned Process D.

Process 6: Introducing the amino protective group

The compound (IIId) or its ester or a salt thereof can be prepared by reacting the compound (IIIc) or its ester or a salt thereof with the introducing agent of amino protective group.

Suitable introducing agent of amino protective group may include an acylating agent.

The reaction is usually carried out in a solvent such as water, methanol, ethanol, ethyl acetate, benzene, diethyl ether, chloroform, methylene chloride, N,N-dimethylformamide or any other solvent which does not adversely influence the reaction.

The reaction temperature is not critical and the reaction may be preferably carried out within a temperature range of cooling to ambient temperature.

Process 7: Elimination of amino-protective group

The compound (IIIc) or its ester or a salt thereof can be prepared by subjecting the compound (IIId) or its ester or a salt thereof to elimination reaction of the amino-protective group.

The reaction may be conducted substantially in the same manner as the aforementioned Process D.

Process 8: Carboxy formation

The compound (IIIf) or its salt can be prepared by transforming the esterified carboxy group of the compound (IIIe) or its salt into free carboxy group, respectively.

The reaction may be conducted substantially in the same manner as aforementioned Process F.

Process 9: Introducing lower alkoxycarbonyl group

The compound (IIIh) or its ester or a salt thereof can be prepared by reacting the compound (IIIg) or its ester or a salt thereof with introducing agent of lower alkoxycarbonyl group.

The suitable example of the introducing agent of lower alkoxycarbonyl group may include 2-(lower)alkoxycarbonylimino-2-cyanoacetamide (e.g. 2-ethoxycarbonyloxyimino-2-cyanoacetamide, 2-isobutoxycarbonyloxyimino-2-cyanoacetamide, etc.), di(lower)alkyl 2-(lower)alkoxycarbonyloxyiminomalonate (e.g. diethyl 2-tert-butoxycarbonyloxyiminomalonate, etc.), lower alkyl 2-(lower)alkoxycarbonyloxyimino-2-cyanoacetate (e.g. ethyl 2-isobutoxycarbonyloxyimino-2-cyanoacetate, etc.), lower alkyl 2-(lower)alkoxycarbonyloxyiminoacetoacetate (e.g. ethyl 2-tert-butoxycarbonyloxyiminoacetoacetate, etc.), lower alkoxycarbonyloxyimino-2-phenylacetonitrile (e.g. tert-butoxycarbonyloxyimino-2-phenylacetonitrile, etc.) or the like.

The reaction is usually carried out in a solvent such as water, methanol, ethanol, acetone, benzene, diethyl ether, tetrahydrofuran, chloroform, methylene chloride, or any other solvent which does not adversely influence the reaction.

The reaction temperature is not critical, and the reaction may be preferably conducted within a temperature range of cooling to elevated temperature.

This process includes within its scope that the amino for $R^1$ is simultaneously transformed to the alkoxycarbonylamino for $R^1$ in the course of this process or the post-treatment.

Process 10: Elimination of hydroxy-protective group

The compound (IIIj) or its ester or a salt thereof can be prepared by subjecting the compound (IIIi) or its ester or a salt thereof to elimination reaction of the hydroxy protective group in the protected hydroxy group for $R_c^2$.

The reaction may be conducted substantially in the same manner as the aforementioned Process E.

Process 11: Introducing the hydroxy-protective group

The compound (IIIi) or its ester or a salt thereof can be prepared by reacting the compound (IIIj) or its ester or a salt thereof with the introducing agent of hydroxy-protective group.

Suitable introducing agent of the hydroxy-protective group may include an acylating agent.

The reaction can be carried out substantially in the similar manner as aforementioned in Process 6.

This process includes within its scope that the amino for $R^1$ is simultaneously transferred to the protected amino for $R^1$ in the course of this process or the post-treatment.

Following examples are given only for explanation of this invention in more detail.

EXAMPLE A (1) 1,2-Dibromoethane (177 g.) was added dropwise to a stirred mixture of ethyl 2-hydroxyimino-3-oxobutyrate (syn isomer, 100 g.), potassium carbonate (87 g.) and N,N-dimethylformamide (200 ml.) under ice cooling over 10 minutes, and stirred at room temperature for 4 hours. The resultant mixture was filtered and washed with acetone. The filtrate and washings were combined and concentrated in vacuo. After adding water (600 ml.) to the residue, the solution was extracted with methylene chloride three times. The extracts were washed with a saturated aqueous solution of sodium chloride, dried over magnesium sulfate and concentrated in vacuo of give ethyl 2-(2-bromoethoxyimino)-3-oxobutyrate (syn isomer 168 g.), oil.

I.R. $\nu_{max}^{film}$: 1740, 1670, 1500 cm$^{-1}$.

N.M.R. $\delta$(CCl$_4$, ppm): 1.34 (3H, t, J=7 Hz), 2.34 (3H, s), 3.52 (2H, t, J=6 Hz), 4.27 (2H, q, J=7 Hz), 4.48 (2H, t, J=6 Hz).

(2) A mixture of ethyl 2-(2-bromoethoxyimino)-3-oxobutyrate (syn isomer, 168 g.), sulfuryl chloride (87.3 g.) and formic acid (168 ml.) was stirred at 40° C. for 10 minutes and at room temperature for 5.5 hours. After adding water (1 l.) to the resultant solution, the mixture was extracted with methylene chloride. The extract was washed with water, a saturated aqueous solution of sodium bicarbonate and a saturated aqueous solution of sodium chloride in turn, dried over magnesium sulfate, and then concentrated in vacuo to give ethyl 2-(2-bromoethoxyimino)-4-chloro-3-oxobutyrate (syn isomer, 156 g.), oil.

I.R. $\nu_{max}^{film}$: 1735, 1710, 1460, 1435 cm$^{-1}$.

N.M.R. $\delta$(CCl$_4$, ppm): 1.36 (3H, t, J=7 Hz), 3.54 (2H, t, J=6 Hz), 4.1–4.8 (4H, m), 4.48 (2H, s).

(3) A mixture of ethyl 2-(2-bromoethoxyimino)-4-chloro-3-oxobutyrate (syn isomer, 156 g.), thiourea (39.4 g.) sodium acetate trihydrate (70.5 g.), water (300 ml.) and ethanol (500 ml.) was stirred at 40° C. for an hour. The resultant solution was concentrated in vacuo and the resiude was extracted twice with ethyl acetate. The extracts were washed with a saturated aqueous solution of sodium chloride, dried over magnesium sulfate and concentrated in vacuo. After adding diethyl ether (1 l.) to the oily residue, the soluble substance was separated by decantation and the solution was concentrated in vacuo. The residue was crystallized with diisopropyl ether and the precipitates were collected by filtration to give ethyl 2-(2-aminothiazol-4-yl)-2-(2-bromoethoxyimino)acetate (syn isomer, 46.4 g.), mp 111° to 114° C.

I.R. $\nu_{max}^{Nujol}$: 3440, 3250, 3125, 1725, 1535 cm$^{-1}$.

N.M.R. $\delta$(DMSO-d$_6$, ppm): 1.30 (3H, t, J=7 Hz), 3.65 (2H, t, J=6 Hz), 3.8–4.6 (4H, m), 6.94 (1H, s), 7.15 (2H, broad s).

(4) A mixture of acetic anhydride (15.9 g.) and formic acid (7.15 g.) was stirred at 50° C. for an hour. After cooling, ethyl 2-(2-aminothiazol-4-yl)-2-(2-bromoethoxyimino)acetate (syn isomer, 25 g.) was added to the solution and stirred at room temperature for an hour. The resultant solution was poured into water and extracted with ethyl acetate twice. The extracts were washed with a saturated aqueous solution of sodium chloride, a saturated aqueous solution of sodium bicarbonate (three times) and a saturated aqueous solution of sodium chloride in turn, and dried over magnesium sulfate. After concentrating the solution in vacuo, the oily residue was triturated with a mixture of diisopropyl ether and diethyl ether. The precipitates were collected by filtration to give ethyl 2-(2-formamidothiazol-4-yl)-2-(2-bromoethoxyimino)acetate (syn isomer, 16.75 g.), mp. 95° to 98° C.

I.R. $\nu_{max}^{Nujol}$: 3170, 3110, 3060, 1730, 1695 cm$^{-1}$.

N.M.R. $\delta$(DMSO-d$_6$, ppm): 1.34 (3H, t, J=7 Hz), 3.74 (2H, t, J=6 Hz), 4.1–4.6 (4H, m), 7.70 (1H, s), 8.60 (1H, s), 12.67 (1H, s).

(5) Allyl mercaptan (2.12 g.) was added dropwise to a stirred suspension of ethyl 2-(2formamidothiazol-4-yl)-2-(2-bromoethoxyimino)acetate (syn isomer, 5 g.) and potassium carbonate (3.95 g.) in N,N-dimethylformamide (50 ml.) under ice cooling and stirred at the same temperature for 10 minutes and further at room temperature for 5 hours. After adding water (300 ml.) to the resultant solution, the mixture was extracted with ethyl acetate three times. The extracts were washed twice with a saturated aqueous solution of sodium chloride, dried over magnesium sulfate and concentrated in vacuo. The oily residue was subjected to column chromatography on silica gel and eluted with chloroform. The eluate was concentrated in vacuo to give ethyl 2-(2-allylthioethoxyimino)-2-(2-formamidothiazol-4-yl)acetate (syn isomer, 4.0 g.), mp. 62° to 64° C.

I.R. $\nu_{max}^{Nujol}$: 3170, 3110, 3060, 1730, 1695, 1630 cm$^{-1}$.

N.M.R. $\delta$(DMSO-d$_6$, ppm): 1.32 (3H, t, J=7 Hz), 2.77 (2H, t, J=7 Hz), 3.24 (2H, d, J=7 Hz), 4.0–4.7 (4H, m), 4.9–6.2 (3H, m), 7.64 (1H, s), 8.58 (1H, s), 12.64 (1H, broad s).

(6) A mixture of ethyl 2-(2-allylthioethoxyimino)-2-(2-formamidothiazol-4-yl)acetate (syn isomer, 5.1 g.), methanol (37.2 ml.), 1N-aqueous sodium hydroxide (37.2 ml.) and tetrahydrofuran (35 ml.) was stirred at 35° C. for 5.5 hours. After concentrating the resultant solution in vacuo, the residue was washed with ethyl acetate twice. The aqueous solution was adjusted to pH 1 with 10% hydrochloric acid and extracted with ethyl acetate twice. The extract was washed with a saturated aqueous solution of sodium chloride dried over magnesium sulfate and concentrated in vacuo. The residue was triturated with n-hexane and the precipitates were collected by filtration to give 2-(2-allylthioethoxyimino)-2-(2-formamidothiazol-4-yl)acetic acid (syn isomer, 2.03 g.), mp. 70° to 78° C.

I.R $\nu_{max}^{KBr}$: 3030 (broad), 1700 (shoulder), 1630, 1545 cm$^{-1}$.

N.M.R. $\delta$(DMSO-d$_6$, ppm): 2.75 (2H, t, J=6 Hz), 3.24 (2H, d, J=7 Hz), 4.29 (2H, t, J=6 Hz), 4.9–6.2 (3H, m), 7.58 (1H, s), 8.56 (1H, s), 12.68 (1H, broad s).

EXAMPLE B (1) Ethyl 2-hydroxyimino-3-oxobutyrate (syn isomer 40 g.), ethoxyethyl bromide (41.1 g.), potassium carbonate (54.1 g.), N,N-dimethylformamide (65 ml.) and ethylacetate (65 ml.) were treated in a similar manner to that of Example A-(1) to give ethyl 2-(2-ethoxyethoxyimino)-3-oxobutyrate (syn isomer, 56.8 g.).

(2) ethyl 2-(2-ethoxyethoxyimino)-3-oxobutyrate (syn isomer 56 g.), sulfuryl chloride (32.7 g.) and acetic acid (56 ml.) were treated in a similar manner to that of Example A-(2) to give ethyl 4-chloro-2-(2-ethoxyethoxyimino)-3-oxobutyrate (syn isomer, 57.1 g.).

(3) A mixture of ethyl 4-chloro-2-(2-ethoxyethoxyimino)-3-oxobutyrate (syn isomer, 56.5 g.), thiourea (19.4 g.), sodium acetate (20.9 g.), ethanol (140 ml.) and water (140 ml.) was stirred at 40° C. for 5 hours. After removing the ethanol from the resultant solution in vacuo, the aqueous solution was adjusted to pH 6.5 with aqueous sodium bicarbonate and then extracted with ethyl acetate. Conc. hydrochloric acid was added to the stirred ethyl acetate extract under ice-cooling to form the precipitates. The precipitates were collected by filtration washed with chilled water and diethyl ether in turn and dried over phosphorus pentoxide under reduced pressure to give ethyl 2-(2-aminothiazol-4-yl)-2-(2-ethoxyethoxyimino)acetate hydrochloride (syn isomer, 23 g.).

I.R. $\nu_{max}^{Nujol}$: 3400, 3220, 3100, 1725, 1630 cm$^{-1}$.

N.M.R. δ(DMSO-d$_6$, ppm): 1.04 (3H, t, J=7 Hz), 1.24 (3H, t, J=7 Hz), 3.4 (2H, q, J=7 Hz), 3.62 (2H, t, J=4 Hz), 4.24 (2H, t, J=4 Hz), 4.32 (2H, q, J=7 Hz), 7.16 (1H, s), 7.88 (2H. broad s).

(4) A suspension of ethyl 2-(2-aminothiazol-4-yl)-2-(2-ethoxyethoxyimino)acetate hydrochloride (syn isomer, 16.9 g.) in a mixture of water (170 ml.) and ethyl acetate (200 ml.) was adjusted to pH 6.5 with sodium bicarbonate and the ethyl acetate layer was separated. The aqueous layer was extracted with ethyl acetate (100 ml.), and the exacts were combined together, washed with a saturated aqueous solution of sodium chloride, dried and then concentrated in vacuo. The oily residue was triturated with n-hexane. The precipitates were collected by filtration and washed with n-hexane to give ethyl 2-(2-aminothiazol-4-yl)-2-(2-ethoxyethoxyimino)acetate (syn isomer, 13 g.).

I.R. $\nu_{max}^{Nujol}$: 3450, 3350, 3150, 3100, 1730, 1720, 1620 cm$^{-1}$.

N.M.R. δ(DMSO-d$_6$, ppm): 1.10 (3H, t, J=7 Hz), 1.28 (3H, t, J=7 Hz), 3.48 (2H, q, J=7 Hz), 3.56 (2H, t, J32 4 Hz), 4.20 (2H, t, J=4 Hz), 4.28 (2H, q, J=7 Hz), 6.86 (1H, s), 7.26 (2H, broad s).

(5) Ethyl 2-(2-aminothiazol-4-yl)-2-(2-ethoxyethoxyimino)acetate (syn isomer, 11.5 g.), acetic anhydride (8.2 g.) and formic acid (3.7 g.) were treated in a similar manner to that of Example A-(4) to give ethyl 2-(2-formamidothiazol-4-yl)-2-(2-ethoxyethoxyimino)acetate (syn isomer, 8.6 g.).

I.R. $\nu_{max}^{Nujol}$: 3170, 3140, 3050, 1730, 1700 cm$^{-1}$.

N.M.R. δ(DMSO-d$_6$, ppm): 1.10 (3H, t, J=7 Hz), 1.28 (3H, t, J=7 Hz), 3.42 (2H, q, J=7 Hz), 3.58 (2H, t, J=4 Hz), 4.23 (2H, t, J=4 Hz), 4.30 (2H, q, J=7 Hz), 7.58 (1H, s), 8.52 (1H, s).

(6) A solution of ethyl 2-(2-formamidothiazol-4-yl)-2-(2-ethoxyethoxyimino)acetate (syn isomer, 4.35 g.) in 1N aqueous sodium hydroxide (33 ml.) was stirred below 10° C. for 3 hours. The resultant solution was adjusted to pH 7.0 with conc. hydrochloric acid under ice cooling and washed with ethyl acetate. To the aqueous solution was added ethyl acetate and adjusted to pH 1.5 with hydrochloric acid under ice cooling. The ethyl acetate layer was separated and the aqueous layer was extracted with ethyl acetate. The extracts were combined together, washed with a saturated aqueous solution of sodium chloride, dried and then concentrated in vacuo. The oily residue was dissolved in diethyl ether and n-hexane was added to the solution until the solution became clear. The solution was stirred for an hour, and the precipitates were collected by filtration and washed with n-hexane to give 2-(2-ethoxyethoxyimino)-2-(2-formamidothiazol-4-yl)acetic acid (syn isomer, 3.2 g.).

I.R. $\nu_{max}^{Nujol}$: 3350, 3140, 1740, 1700 cm$^{-1}$.

N.M.R. δ(DMSO-d$_6$, ppm): 1.14 (3H, t, J=7 Hz), 3.50 (2H, q, J=7 Hz), 3.66 (2H, t, J=4 Hz), 4.30 (2H, t, J=4 Hz), 7.58 (1H, s), 8.58 (1H, s).

EXAMPLE C (1) A mixture of ethyl 2-hydroxyimino-3-oxobutyrate (syn isomer, 15.7 g.), 2-bromoethyl benzoate (27.5 g.), potassium carbonate (20.7 g.), N,N-dimethylformamide (25 ml.) and ethyl acetate (25 ml.) was treated in a similar manner to that of Example A-(1) to give ethyl 2-(2-benzoyloxyethoxyimino)-3-oxobutyrate (syn isomer, 28 g.).

(2) A solution of 2-(2-benzoyloxyethoxyimino)-3-oxobutyrate (syn isomer, 28 g.), sulfuryl chloride (13.5 g.) and acetic acid (30 ml.) was treated in a similar manner to that of Example A-(2) to give ethyl 2-(2-benzoyloxyethoxyimino)-4-chloro-3-oxobutyrate (syn isomer, 29 g.).

(3) Ethyl 2-(2-benzoyloxyethoxyimino)-4-chloro-3-oxobutyrate (syn isomer, 29 g.), thiourea (7.76 g.), sodium acetate (8.37 g.), water (75 ml.) and ethanol (75 ml.) were treated in a similar manner to that of Example A-(3) to give ethyl 2-(2-aminothiazol-4-yl)-2-(2-benzoyloxyethoxyimino)acetate (syn isomer, 9 g.).

N.M.R. δ(DMSO-d$_6$, ppm): 1.28 (3H, t, J=7 Hz), 4.34 (2H, q, J=7 Hz), 4.56 (4H, m), 6.44 (2H, broad s), 6.68 (1H, s), 7.68–7.34 (3H, m), 8.06 (2H, d, d, J=8 Hz, 2 Hz).

(4) A solution of ethyl 2-(2-aminothiazol-4-yl)-2-(2-benzoyloxyethoxyimino)acetate (syn isomer, 8.5 g.) in a mixture of 1N aqueous sodium hydroxide (34 ml.), methanol (40 ml.) and tetrahydrofuran (40 ml.) was treated in a similar manner to that of Example C-(4) to give 2-(2-aminothiazol-4-yl)-2-(2-hydroxyethoxyimino)acetic acid (syn isomer, 3.3 g.).

I.R. $\nu_{max}^{Nujol}$: 3350, 3075, 1680, 1620 cm$^{-1}$.

N.M.R. δ(DMSO-d$_6$, ppm) : 3.64 (2H, t, J=5 Hz), 4.10 (2H, t, J=5 Hz), 6.84 (1H, s), 7.16 (2H, m).

(5) A solution of formic acid (1.6 g.) and acetic anhydride (3.6 g.) was stirred at 50° C. for an hour. After cooling, 2-(2-aminothiazol-4-yl)-2-(2-hydroxyethoxyimino)acetic acid (syn isomer, 1 g.) was added to the solution and stirred at room temperature for 3 hours. Diisopropyl ether was added to the resultant solution, and the precipitates were filtered out. The filtrate was concentrated in vacuo, and the residue was pulverized with diisopropyl ether. The precipitates were collected by filtration to give 2-(2-formamidothiazol-4-yl)-2-(2-formyloxyethoxyimino)acetic acid (syn isomer, 0.7 g.).

I.R. $\nu_{max}^{Nujol}$: 3200, 1710, 1690 cm$^{-1}$.

N.M.R. δ(DMSO-d$_6$, ppm) : 4.38 (4H, s), 7.58 (1H, s), 8.26 (1H, s), 8.54 (1H, s).

EXAMPLE D

To a solution of 2-(2-formamidiothiazol-4-yl)-oxalic acid (4.63 g.) and sodium bicarbonate (1.95 g.) in water (230 ml.) was added 2-aminooxyacetamide (2.5 g.) and the mixture was stirred at room temperature for 6 hours while keeping at pH 5. After adjusting the solution to pH 1.5 with 10% hydrochloric acid, the precipitates were collected by filtration, washed with water and dried to give 2-(2-formamidothiazol-4-yl)-2-carbamoylmethoxyiminoacetic acid (syn isomer, 3.6 g.), mp 195° C. (dec.).

I.R. $\nu_{max}^{Nujol}$: 3490, 3180, 3110, 1725, 1685, 1660 cm$^{-1}$.

N.M.R. δ(DMSO-d$_6$, ppm) : 4.58 (2H, s), 7.01 (1H, broad s), 7.47 (1H, broad s), 7.64 (1H, s), 8.57 (1H, s), 12.70 (1H, broad s).

EXAMPLE E (1) Phenolphthalein (2 drops) was added to a suspension of 2-aminooxyethylamine dihydrochloride (1.0 g.) in methanol (10 ml.), and adjusted to pH 6 with 1N sodium methoxide. After removing the precipitates from the solution, 2-(2-formamidothiazol-4-yl)oxalic ) acid (1.04 g.) was added to the filtrate at room temperature and stirred at the same temperature for 5 hours. The precipitates were collected by filtration to give 2-(2-formamidothiazol-4-yl)-2-(2-aminoethoxyimino)acetic acid (syn isomer, 0.80 g.).

I.R. $\nu_{max}^{Nujol}$: 3100, 1680, 1590 cm$^{-1}$.

N.M.R. δ(DSMO-d$_6$, ppm) : 3.53 (2H, m), 4.17 (2H, broad s), 7.37 (1H, s), 8.47 (1H, s).

(2) A mixture of 2-(2-formamidothiazol-4-yl)-2-(2-aminoethoxyimino)acetic acid (syn isomer, 0.80 g.) and triethylamine (0.45 g.), in a solution of a saturated aqueous solution of sodium bicarbonate (4 ml.), tetrahydrofuran (35 ml.) and water (25 ml.) was adjusted to pH 8.5 with hydrochloric acid. 2-Phenyl-2-(tert-butoxycarbonyloxyimino)acetonitrile (0.77 g.) was added to the stirred solution and stirred at room temperature for 3 hours. After distilling off tetrahydrofuran from the resultant solution, the aqueous solution was washed with diethyl ether, and adjusted to pH 1.5 with 85% phosphoric acid. The solution was extracted with ethyl acetate (50 ml.), and the extract was washed with a saturated aqueous solution of sodium chloride (10 ml.), dried over magnesium sulfate and concentrated under reduced pressure to give 2-(2-formamidothiazol-4-yl)-2-(2-tert-butoxycarbonylaminoethoxyimino)acetic acid (syn isomer, 0.40 g.).

EXAMPLE F

A mixture of 2-(2-formamidothiazol-4-yl)oxalic acid (1.59 g.), tert-butyl N-aminooxyethylcarbamate (1.40 g.) and methanol (25 ml.) was stirred at room temperature for 6 hours. After removal of methanol from the resultant solution under reduced pressure, the residue was pulverized with diethyl ether. The precipitates were collected by filtration to give 2-(2-formamidothiazol-4-yl)-2-(2-tert-butoxycarbonlyaminoethoxyimino)acetic acid (syn isomer, 2.20 g.).

I.R. $\nu_{max}^{Nujol}$: 3140, 1698, 1604 cm$^{-1}$.

N.M.R. δ(DMSO-d$_6$, ppm) : 1.37 (9H, s), 3.20 (2H, m), 3.97 (2H, m), 6.73 (1H, broad s), 7.33 (1H, s), 8.50 (1H, s).

EXAMPLE G (1) Potassium carbonate (4.84 g.) was added to a stirred solution of ethyl 2-(2-tritylaminothiazol-4-yl)-2-hydroxyiminoacetate (syn isomer, 10 g.) in N,N-dimethylformamide (22.0 ml.). Chloracetonitrile (2.64 g.) was added dropwise to the solution under nitrogen atmosphere and stirred at room temperature for 5 hours. After removing the insoluble substance from the resultant mixture by filtration, water (300 ml.) was added to the filtrate and extracted with ethyl acetate (300 ml.). The extract was washed with a saturated aqueous solution of sodium chloride, dried over magnesium sulfate, treated with activated charcoal and concentrated in vacuo. The residue was pulverized with a mixture of n-hexane, ethyl acetate and acetone (4:4:1) and then the precipitates were collected by filtration and washed with n-hexane to give ethyl 2-(2-tritylaminothiazol-4-yl)-2-cyanomethoxyiminoacetate (syn isomer, 9.58 g.).

I.R. $\nu_{max}^{Nujol}$: 3400, 2200, 1720 cm$-1$.

N.M.R. δ(DMSO-d$_6$, ppm) : 1.13 (3H, t, J=7.5 Hz), 4.06 (2H, q, J=7.5 Hz), 5.05 (2H, s), 7.13 (1H, s), 7.13–7.62 (15H, m), 8.92 (1H, s).

(2) A solution of ethyl 2-(2-tritylaminothiazol-4-yl)-2-cyanomethoxyiminoacetate (syn isomer, 4.96 g.) in 90% aqueous formic acid (50 ml.) was stirred at room temperature for 40 minutes. The precipitates were filtered off and washed with diisopropyl ether (20 ml.). The filtrate and the washings were combined together and evaporated in vacuo below 40° C. The residue was washed with benzene (85 ml.) and dried to give ethyl 2-(2-aminothiazol-4-yl)-2-cycanomethoxyiminoacetate (syn isomer, 1.5 g.), mp. 167° to 168° C.

I.R. $\nu_{max}^{Nujol}$: 3440, 3260, 3120, 1730, 1625cm$^{-1}$.

N.M.R. δ(DMSO-d$_6$, ppm) : 1.32 (3H, t, J=6 Hz), 4.36 (2H, q, J=6 Hz), 5.10 (2H, s), 7.07 (1H, s), 7.37 (2H, s).

EXAMPLE H (1) Hydrazine hydrate (3.7 g.) was added to a solution of N-cyanomethoxyphthalimide (15.2 g) in ethanol (100 ml) at 50° C. and stirred at 65° to 70° C. for 15 minutes. To the solution were added conc.hydrochloric acid (7.5 ml) and water (10 ml). The insoluable substance was removed by filtration, and the filtrate was adjusted to pH 7 with 10% aqueous sodium hydroxide. 2-(2-Formamidothiazol-4-yl)oxalic acid (10 g) was added to the solution and adjusted to pH 4 to 4.5 with a saturated aqueous solution of sodium bicarbonate and stirred for 2 hours. After removing ethanol from the resultant solution in vacuo, ethyl acetate was added to the residue and adjusted to pH 7 with a saturated aqueous solution of sodium bicarbonate. The aqueous layer was separated, adjusted to pH 2 with 10% hydrochloric acid and extracted with ethyl acetate. The extract was washed with a saturated aqueous solution of sodium chloride, dried over magnesium sulfate and concentrated in vacuo. The residue was pulverized with diisopropyl ether to give 2-(2-formamidothiazol-4-yl)-2-cyanomethoxyiminoacetic acid (syn isomer, 8.3 g).

I.R. $\nu_{max}^{Nujol}$: 3260, 1680, 1595, 1540cm$^{-1}$.

N.M.R. δ(DMSO-d$_6$, ppm): 5.20 (2H, s), 7.73 (1H, s), 8.62 (1H, s).

(2) A solution of 2-(2-formamidothiazol-4-yl)-2-cyanomethoxyiminoacetic acid (syn isomer, 2.54 g) and conc. hydrochloric acid (3 ml) in methanol (30 ml) was stirred at room temperature for an hour. After removing methanol from the resultant mixture in vacuo, water was added to the residue and adjusted to pH 3.3 with an aqueous solution of sodium bicarbonate under ice-cooling. The precipitates were collected by filtration to give 2-(2-aminothiazol-4-yl)-2-cyanomethoxyiminoacetic acid (syn isomer, 2.1 g)

I.R. $\nu_{max}^{Nujol}$: 3250, 1660, 1620 cm$^{-1}$.

N.M.R. δ(DMSO-d$_6$, ppm) : 5.10 (2H, s), 7.03 (1H, s).

EXAMPLE I

Sodium azide (14.87 g.) was added to a solution of 2-(2-formamidothiazol-4-yl)-2-(2- bromoethoxyimino)acetic acid (syn isomer, 15.7 g.) in N,N-dimethylformamide (100 ml.) and water (75 ml.), and stirred at room temperature for 2 days. To the resultant solution was added water (25 ml.) and adjusted to pH 8.0 with a saturated aqueous solution of sodium bicarbonate. The solution was washed with ethyl acetate (250 ml.). The solution was adjusted to pH 2.5 and extracted with ethyl acetate (350 ml.). The extract was washed with a saturated aqueous solution of sodium chloride, dried over magnesium sulfate and concentrated in vacuo. The residue was recrystalized from a solution of acetone and methylene chloride (3:1) repeatedly. The precipitates were collected by filtration to give 2-(2-formamidothiazol-4-yl)-2-(2-azidoethoxyimino)acetic acid (syn isomer, 4.95 g.).

I.R. $\nu_{max}^{Nujol}$: 3180, 2110, 1690 cm$^{-1}$.

N.M.R. $\delta$(DMSO-d$_6$, ppm): 3.59 (2H, t, J=5 Hz), 4.32 (2H, t, J=5 Hz), 7.58 (1H, s), 8.54 (1H, s).

EXAMPLE 1

Phosphoryl chloride (1.4 g.) was added dropwise to a stirred solution of 2-(2-aminothiazol-4-yl)-2-(2-hydroxyethoxyimino)acetic acid (syn isomer, 1.7 g.) in dry tetrahydrofuran (17.0 ml.) at $-3°$ C. and stirred at the same temperature for 20 minutes. Trimethylsilylacetamide (2.1 g.) was added to the solution and stirred for 20 minutes. Phosphoryl chloride (1.4 g.) was added to the solution and stirred for 20 minutes. Dry N,N-dimethylformamide (0.7 g.) was added to the solution and stirred at $-3°$ to $3°$ C. for an hour to give an activated acid solution. The solution was added to a solution of 7-aminocephalosporanic acid (2.0 g.) and trimethylsilylacetamide (7.7 g.) in dry ethyl acetate (30 ml.) at $-10°$ C., and stirred at $-10°$ to $-5°$ C. for an hour. Water (20 ml.) was added to the resultant solution and adjusted to pH 7.0 with a saturated aqueous solution of sodium bicarbonate. The aqueous layer was separated, washed with ethyl acetate and adjusted to pH 3.8 with 10% hydrochloric acid. The solution was subjected to column chromatography on nonionic adsorption resin "Diaion HP-2" (Trademark, manufactured by Mitsubishi Chemical Industries Ltd.). The column was washed with water and eluted with 20% isopropyl alcohol. The eluate was concentrated in vacuo and the residue was lyophylized to give 7-[2-(2-aminothiazol-4-yl)-2-(2-hydroxyethoxyimino)acetamido]cephalosporanic acid (syn isomer, 0.73 g.).

I.R. $\nu_{max}^{Nujol}$: 1775, 1735, 1660, 1635 cm$^{-1}$.

N.M.R. $\delta$(DMSO-d$_6$, ppm): 2.08 (3H, s), 3.57 (2H, m), 3.83–4.30 (4H, m), 4.87 (2H, m), 5.17 (1H, d, J=4.0 Hz), 5.80 (1H, d,d, J=4.0 Hz, 8.0 Hz), 6.77 (1H, s), 9.70 (1H, d, J=8.0 Hz).

EXAMPLE 2

(1) N,N-Dimethylformamide (0.4 g.), dry ethyl acetate (11.6 ml.), phosphoryl chloride (0.9 g.) and 2-(2-formamidothiazol-4-yl)-2-(2-formyloxyethoxyimino)acetic acid (syn isomer, 1.6 g.) were treated in a similar manner to that of Example 1-(1) to give an activated acid solution. On the other hand, a suspension of 7-amino-3-carbamoyloxymethyl-3-cephem-4-carboxylic acid (1.5 g.) in a mixture of water (10 ml.) and acetone (20 ml.) was adjusted to pH 8.0 with triethylamine at $-3°$ C. The activated acid solution was added to the stirred solution over 15 minutes while keeping at pH 7.5 to 8.0, and stirred at $-3°$ to $3°$ C. for 30 minutes. After removing the solvent from the resultant solution in vacuo at pH 7.0, water (20 ml.) was added to the residue. The aqueous solution was washed with ethyl acetate and diethyl ether in turn, and the remaining organic solvent was removed from the solution by bubbling nitrogen gas. After adjusting the solution to pH 2.5 with 10% hydrochloric acid, the precipitates were collected by filtration, washed with water and dried over phosphorous pentoxide under reduced pressure to give 7-{2-(2-formamidothiazol-4-yl)-2-(2-formyloxyethoxyimino)-acetamido}-3-carbamoyloxymethyl-3-cephem-4-carboxylic acid (syn isomer, 1.05 g.). The mother liquid was extracted with ethyl acetate. The extract was washed with a saturated aqueous solution of sodium chloride, dried over magnesium sulfate and concentrated in vacuo. The residue was pulverized with diisopropyl ether. The pricipitates were collected by filtration, washed with diisopropyl ether and dried to give the same object compound (0.6 g.). Total yield 1.65 g.

I.R. $\nu_{max}^{Nujol}$: 1770, 1710, 1670 cm$^{-1}$.

N.M.R. $\delta$(DMSO-d$_6$, ppm): 3.50 (2H, m), 4.10–4.60 (4H, m), 4.79 (2H, m), 5.16 (1H, d, J=5.0 Hz), 5.81 (1H, d,d, J=5.0 Hz, 8.0 Hz), 6.58 (2H, broad s), 7.47 (1H, s), 8.28 (1H, s), 8.55 (1H, s).

(2) A mixture of 7-[2-(2-formamidothiazol-4-yl)-2-(2-formyloxyethoxyimino)acetamido]-3-carbamoyloxymethyl-3-cephem-4-carboxylic acid (syn isomer, 1.5 g.), conc. hydrochloric acid (0.6 g.), tetrahydrofuran (7.5 ml.) and methanol (15.0 ml.) was stirred at room temperature for 6 hours. After concentrating the resultant solution in vacuo, the residue was pulverized with a mixture of methanol and diisopropyl ether. The precipitates were collected by filtration, washed with diisopropyl ether and dried to give 7-[2-(2-aminothiazol-4-yl)-2-(2-hydroxyethoxyimino)acetamido]-3-carbamoyloxymethyl-3-cephem-4-carboxylic acid hydrochloride (syn isomer, 1.36 g.).

I.R. $\nu_{max}^{Nujol}$: 1765, 1660 cm$^{-1}$.

N.M.R. $\delta$(DMSO-d$_6$, ppm): 3.25–3.96 (4H, m), 4.19 (2H, m), 4.50–5.04 (2H, m), 5.20 (1H, d, J=4.0 Hz), 5.83 (1H, d,d, J=4.0 Hz, 8.0 Hz), 6.98 (1H, s), 9.79 (1H, d, J=8.0 Hz).

EXAMPLE 3

(1) Phosphoryl chloride (0.96 g.), N,N-dimethylformamide (0.459 g.), tetrahydrofuran (12 ml.) and 2-(2-formamidothiazol-4-yl)-2-carbamoylmethoxyiminoacetic acid (syn isomer, 1.2 g.) were treated in a similar manner to that of Example 1-(1) to give an activated acid solution. After a suspension of 7-amino-3-(1,3,4-thiadiazol-2-yl)thiomethyl-3-cephem-4-carboxylic acid (1.75 g.) in 50% aqueous acetone (16 ml.) was adjusted to pH 7 to 8.5 with triethylamine, the activated acid solution was added to the stirred solution at $-5°$ to $0°$ C. while keeping at pH 6.5 to 7.5 and stirred at the same temperature for 30 minutes. After removing the solvent from the resultant solution in vacuo, ethyl acetate was added to the residue. The solution was adjusted to pH 1.5 with 10% hydrochloric acid and the insoluble substance was filtered off. The filtrate was extracted with ethyl acetate. The extract was washed with a saturated aqueous solution of sodium chloride, dried over magnesium sulfate and concentrated in vacuo. The residue was pulverized with diethyl ether to give 7-[2-(2-formamidothiazol-4-yl)-2-cyanomethoxyiminoacetamido]-3-(1,3,4-thiadiazol-2-yl)thiomethyl-3-cephem-4-carboxylic acid (syn isomer, 0.87 g.).

I.R. $\nu_{max}^{Nujol}$: 3200 (broad), 1780, 1680, 1545 cm$^{-1}$.

N.M.R. $\delta$(DMSO-d$_6$, ppm): 3.74 (2H, q, J=18 Hz), 4.48 (2H, q, J=12 Hz), 5.12 (2H, s), 5.22 (1H, d, J=5 Hz), 5.85 (1H, d,d, J=5 Hz, 8 Hz), 7.58 (1H, s), 8.57 (1H, s), 9.59 (1H, s), 9.90 (1H, d, J=8 Hz), 12.76 (1H, s)

(2) A mixture of 7-[2-(2-formamidothiazol-4-yl)-2-cyanomethoxyiminoacetamido]-3-(1,3,4-thiadiazol-2-yl)thiomethyl-3-cephem-4-carboxylic acid (syn isomer, 0.8 g.), methanol (12 ml.), conc hydrochloric acid (0.55 g.) and tetrahydrofuran (10 ml.) was stirred at room temperature for 3 hours. After concentrating the resultant solution in vacuo, the residue was dissolved in an aqueous solution of sodium bicarbonate. The solution was adjusted to pH 3.5 with 10% hydrochloric acid and stirred for 30 minutes. The precipitates were collected by filtration, washed with water and dried to give 7-[2-(2-aminothiazol-4-yl)-2-cyanomethoxyiminoacetamido]-3-(1,3,4-thiadiazol-2-yl)thiomethyl-3-cephem-4-carboxylic acid (syn isomer, 0.56 g.).

I.R. $\nu_{max}^{Nujol}$: 3360, 3230, 3050, 1780, 1680 cm$^{-1}$.

N.M.R. $\delta$(DMSO-d$_6$, ppm): 3.72 (2H, q, J=18 Hz), 4.45 (2H, q, J=14 Hz), 5.02 (2H, s), 5.17 (1H, d, J=5 Hz), 5.78 (1H, d,d, J=5 Hz, 8 Hz), 6.90 (1H, s), 7.30 (2H, broad s), 9.57 (1H, s), 9.83 (1H, d, J=8 Hz).

EXAMPLE 4

(1) Dry N,N-dimethylformamide (1.2 g.), phosphoryl chloride (2.5 g.), 2-(2-formamidothiazol-4-yl)-2-(2-formyloxyethoxyimino)acetic acid (syn isomer, 3.8 g.) and dry ethyl acetate (49.7 ml.) were treated in a similar manner to that of Example 1-(1) to give an activated acid solution. The solution was added to a solution of 7-amino-3-(1,3,4-thiadiazol-2-yl)thiomethyl-3-cephem-4-carboxylic acid (4.4 g.) and trimethylacetamide (12.3 g.) in dry ethyl acetate (90 ml.) at −10° C., and stirred at −5° to −10° C. for an hour. Water (50 ml.) was added to the resultant solution and allowed to stand at room temperature. The ethyl acetate layer was separated, washed with a saturated aqueous solution of sodium chloride and dried over magnesium sulfate. After concentrating the solution in vacuo, the residue was pulverized with diisopropyl ether. The precipitates were collected by filtration, washed with diisopropyl ether and dried to give 7-[2-(2-formamidothiazol-4-yl)-2-(2-formyloxyethoxyimino)acetamido]-3-(1,3,4-thiadiazol-2-yl)thiomethyl-3-cephem-4-carboxylic acid (syn isomer, 2.5 g.).

I.R. $\nu_{max}^{Nujol}$: 3180, 1775, 1673 cm$^{-1}$.

N.M.R. $\delta$(DMSO-d$_6$, ppm): 3.75 (2H, m), 4.25–4.65 (6H, m), 5.22 (1H, d, J=5.0 Hz), 5.88 (1H, d,d, J=5.0 Hz, 9.0 Hz), 7.49 (1H, s), 8.26 (1H, s), 8.57 (1H, s), 9.59 (1H, s), 9.71 (1H, d, J=9.0 Hz).

(2) A mixture of 7-[2-(2-formamidothiazol-4-yl)-2-(2-formyloxyethoxyimino)acetamido]-3-(1,3,4-thiadiazol-2-yl)thiomethyl-3-cephem-4-carboxylic acid (syn isomer, 3.1 g.), conc. hydrochloric acid (1.35 g.), tetrahydrofuran (23.0 ml.), and methanol (23.0 ml.) was stirred at room temperature for 6.5 hours. After concentrating the resultant solution in vacuo, methanol (50 ml.) was added to the residue. After concentrating the solution to a half volume of the initial, the precipitates were collected by filtration, washed with diethyl ether and dried to give 7-[2-(2-aminothiazol-4-yl)-2-(2-hydroxyethoxyimino)acetamido]-3-(1,3,4-thiadiazol-2-yl)thiomethyl-3-cephem-4-carboxylic acid hydrochloride (syn isomer, 0.71 g.).

I.R. $\nu_{max}^{Nujol}$: 3270, 3080, 1763, 1715, 1665, 1645 cm$^{-1}$.

N.M.R. $\delta$(DMSO-d$_6$, ppm): 3.32–3.95 (4H, m), 3.95–4.70 (4H, m), 5.20 (1H, d, J=4.0 Hz), 5.79 (1H, d,d, J=4.0 Hz, 8.0 Hz), 7.01 (1H, s), 7.42 (2H, broad s), 9.60 (1H, s), 9.82 (1H, d, J=8.0 Hz).

(3) A solution of 7-[2-(2-aminothiazol-4-yl)-2-(2-hydroxyethoxyimino)acetamido]-3-(1,3,4-thiadiazol-2-yl)thiomethyl-3-cephem-4-carboxylic acid hydrochloride (syn isomer, 10.5 g.) in water (300 ml.) was adjusted to pH 4.0 and subjected to column chromatography on nonionic adsorption resin "Diaion HP-20" (trademark, manufactured by Mitsubishi Chemical Industries Ltd.). After washing the column with water (200 ml.), the object compound was eluted with 20% isopropyl alcohol. The eluate was lyophilized to give 7-[2-(2-aminothiazol-4-yl)-2-(2-hydroxyethoxyimino)acetamido]-3-(1,3,4-thiadiazol-2-yl)thiomethyl-3-cephem-4-carboxylic acid (syn isomer, 7.2 g.).

I.R. $\nu_{max}^{Nujol}$: 3200, 1765, 1670, 1600 cm$^{-1}$.

N.M.R. $\delta$(DMSO-d$_6$, ppm): 3.10–3.88 (4H, m), 4.07 (2H, m), 4.54 (2H, q, J=13.0 Hz), 5.05 (1H, d, J=5.0 Hz), 5.65 (1H, dd, J=5.0 Hz, 9.0 Hz), 6.75 (1H, s), 7.30 (2H, broad s), 9.49 (1H, d, J=9.0 Hz), 9.55 (1H, s).

EXAMPLE 5

(1) 2-(2-Formamidothiazol-4-yl)-2-(2-azidoethoxyimino)acetic acid (syn isomer, 0.70 g.), N,N-dimethylformamide (0.21 ml.), phosphoryl chloride (0.4 g.) and ethyl acetate (15.8 ml.) were treated in a similar manner to that of Example 1-(1) to give an activated acid solution. The solution was added to a solution of 7-amino-3-(1,3,4-thiadiazol-2-yl)thiomethyl-3-cephem-4-carboxylic acid (0.74 g.) and trimethylsilylacetamide (2.0 g.) in ethyl acetate (15 ml.) at −10° to −15° C. and stirred at the same temperature for an hour. After adding water (30 ml.) to the resultant solution, the organic layer was separated, washed with a saturated aqueous solution of sodium chloride dried over magnesium sulfate and evaporated in vacuo to give 7-[2-(2-formamidothiazol-4-yl)-2-(2-azidoethoxyimino)acetamido]-3-(1,3,4-thiadiazol-2-yl)thiomethyl-3-cephem-4-carboxylic acid (syn isomer, 1.08 g.).

I.R. $\nu_{max}^{Nujol}$: 3180, 2100, 1760, 1680, 1640 cm$^{-1}$.

N.M.R. $\delta$(DMSO-d$_6$, ppm): 3.50–3.90 (4H, m), 4.01–4.80 (4H, m), 5.23 (1H, d, J=5 Hz), 5.88 (1H, d,d, J=5 Hz, 8 Hz), 7.52 (1H, s), 8.57 (1H, s), 9.60 (1H, s), 9.72 (1H, d, J=8 Hz).

(2) A mixture of 7-[2-(2-formamidothiazol-4-yl)-2-(2-azidoethoxyimino)acetamido]-3-(1,3,4-thiadiazol-2-yl)thiomethyl-3-cephem-4-carboxylic acid (syn isomer, 0.9 g.), conc. hydrochloric acid (0.2 g.), methanol (10 ml.) and tetrahydrofuran (4 ml.) was stirred at room temperature for 5 hours. After concentrating the resultant solution in vacuo, the residue was pulverized with a mixture of disopropyl ether and ethyl acetate (30 ml. 5:1 v/v). The precipitates were collected by filtration, washed with diisopropyl ether and dried to give 7-[2-(2-aminothiazol-4-yl)-2-(2-azidoethoxyimino)acetamido]-3-(1,3,4-thiadiazol-2-yl)thiomethyl-3-cephem-4-carboxylic acid hydrochloride (syn isomer, 0.8 g.).

I.R. $\nu_{max}^{Nujol}$: 3200, 2120, 1780, 1720, 1680, 1635 cm$^{-1}$.

N.M.R. $\delta$(DMSO-d$_6$, ppm): 3.40–3.93 (4H, m), 4.13–4.70 (4H, m), 5.23 (1H, d, J=5 Hz), 5.80 (1H, d,d, J=5 Hz, 8 Hz), 7.05 (1H, s), 7.40 (2H, broad s), 9.60 (1H, s), 9.87 (1H, d, J=8 Hz).

EXAMPLE 6

(1) N,N-Dimethylformamide (0.207 g.), phosphoryl chloride (0.436 g.), 2-(2-formamidothiazol-4-yl)-2-(2-azidoethoxyimino)acetic acid (syn isomer, 0.65 g.), 7-amino-3-(1-methyl-1H-tetrazol-5-yl)thiomethyl-3-cephem-4-carboxylic acid (0.85 g.), trimethylsilylacetamide (2.71 g.) and ethyl acetate (20 ml.) were treated in a similar manner to that of Example 5-(1) to give 7-[2-(2-formamidothiazol-4-yl)-2-(2-azidoethoxyimino)acetamido]-3-(1-methyl-1H-tetrazol-5-yl)thiomethyl-3-cephem-4-carboxylic acid (syn isomer, 0.80 g.).

I.R. $\nu_{max}^{Nujol}$: 3170, 2100, 1775, 1670 cm$^{-1}$.

N.M.R. $\delta$(DMSO-d$_6$, ppm): 3.40–3.93 (4H, m), 3.97 (3H, s), 4.17–4.53 (4H, m), 5.19 (1H, d, J=5 Hz), 5.86 (1H, d,d, J=5 Hz, 8 Hz), 7.50 (1H, s), 8.57 (1H, s), 9.70 (1H, d, J=8 Hz).

(2) A mixture of 7-[2-(2-formamidothiazol-4-yl)-2-(2-azidoethoxyimino)acetamido]-3-(1-methyl-1H-tetrazol-5-yl)thiomethyl-3-cephem-4-carboxylic acid (syn isomer, 0.70 g.), 10% palladium carbon (0.85 g.) and acetic acid (10 ml.) was subjected to catalytic reduction under ordinary pressure at room temperature for 13 hours. The resultant mixture was filtered, and the filtrate was concentrated in vacuo. The residue was stirred in diisopropyl ether (30 ml.) and methanol (10 ml.) for an hour. The precipitates were collected by filtration, washed with diisopropyl ether and dried to give 7-[2-(2-formamidothiazol-4-yl)-2-(2-aminoethoxyimino)acetamido]-3-(1-methyl-1H-tetrazol-5-yl)thiomethyl-3-cephem-4-carboxylic acid (syn isomer, 0.35 g.).

I.R. $\nu_{max}^{Nujol}$: 3170, 1760, 1665 cm$^{-1}$.

N.M.R. $\delta$(DMSO-d$_6$, ppm): 3.10–3.77 (4H, m), 3.93 (3H, s), 4.10–4.70 (4H, m), 5.04 (1H, d, J=5 Hz), 5.58 (1H, d,d, J=5 Hz, 8 Hz), 6.10 (2H, broad s), 7.50 (1H, s), 8.55 (1H, s), 9.57 (1H, d, J=8 Hz).

(3) A mixture of 7-[2-(2-formamidothiazol-4-yl)-2-(2-aminoethoxyimino)acetamido]-3-(1-methyl-1H-tetrazol-5-yl)thiomethyl-3-cephem-4-carboxylic acid (syn isomer, 0.30 g.), conc. hydrochloric acid (0.14 g.) and methanol (3.5 ml.) was stirred at room temperature for 7 hours. After concentrating the resultant solution in vacuo, the residue was pulverized with a mixture of diisopropyl ether (10 ml.) and methanol (10 ml.). The precipitates were collected by filtration to give 7-[2-(2-aminothiazol-4-yl)-2-(2-aminoethoxyimino)acetamido]-3-(1-methyl-1H-tetrazol-5-yl)thiomethyl-3-cephem-4-carboxylic acid dihydrochloride (syn isomer, 0.21 g.).

I.R. $\nu_{max}^{Nujol}$: 3160, 1760, 1670, 1625 cm$^{-1}$.

N.M.R. $\delta$(DMSO-d$_6$, ppm): 3.10–3.87 (4H, m), 3.99 (3H, s), 4.34 (4H, m), 5.17 (1H, d, J=5 Hz), 5.80 (1H, d,d, J=5 Hz, 8 Hz), 6.10 (2H, broad s), 7.07 (1H, s), 8.37 (2H, broad s), 9.90 (1H, d, J=8 Hz).

EXAMPLE 7

(1) 2-(2-Formamidothiazol-4-yl)-2-(2-formyloxyethoxyimino)acetic acid (syn isomer, 3.4 g.), 7-amino-3-(1-methyl-1H-tetrazol-5-yl)thiomethyl-3-cephem-4-carboxylic acid (4.3 g.), trimethylsilylacetamide (12.6 g.), dry N,N-dimethylformamide (1.0 g.), phosphoryl chloride (2.0 g.), ethyl acetate (139 ml.) were treated in a similar manner to that of Example 11-(1) to give 7-[2-(2-formamidothiazol-4-yl)-2-(2-formyloxyethoxyimino)acetamido]-3-(1-methyl-1H-tetrazol-5-yl)thiomethyl-3-cephem-4-carboxylic acid (syn isomer, 2.47 g.).

I.R. $\nu_{max}^{Nujol}$: 3160, 1775, 1710, 1670 cm$^{-1}$.

N.M.R. $\delta$(DMSO-d$_6$, ppm): 3.71 (2H, q, J=18.0 Hz), 3.96 (3H, s), 4.00–4.54 (6H, m), 5.16 (1H, d, J=4.5 Hz), 5.84 (1H, d,d, J=4.5 Hz, 9.0 Hz), 7.45 (1H, s), 8.24 (1H, s), 8.53 (1H, s), 9.70 (1H, d, J=9.0 Hz).

(2) A mixture of 7-[2-(2-formamidothiazol-4-yl)-2-(2-formyloxyethoxyimino)acetamido]-3-(1-methyl-1H-tetrazol-5-yl)thiomethyl-3-cephem-4-carboxylic acid (syn isomer, 2.3 g.), conc. hydrochloric acid (1.6 g.), tetrahydrofuran (17.0 ml.) and methanol (17.0 ml.) was stirred at room temperature for 7.6 hours. After concentrating the resultant solution in vacuo, the residue was pulverized with a mixture of methanol and diisopropyl ether. The precipitates were collected by filtration, washed with diisopropyl ether and dried to give 7-[2-(2-aminothiazol-4-yl)-2-(2-hydroxyethoxyimino)acetamido]-3-(1-methyl-1H-tetrazol-5-yl)thiomethyl-3-cephem-4-carboxylic acid hydrochloride (syn isomer, 2.3 g.). Water (40 ml.) was added to the product and adjusted to pH 7.0 with sodium bicarbonate. After adjusting the solution to pH 4.0 with 1N hydrochloric acid, the solution was subjected to column chromatography on nonionic adsorption resin "Diaion HP-20" (Trademark, manufactured by Mitsubishi Chemical Industries Ltd.). The column was washed with water and eluted with 20% isopropyl alcohol. The eluate was concentrafted in vacuo and lyophilized to give 7-[2-(2-aminothiazol-4-yl)-2-(2-hydroxyethoxyimino)acetamido]-3-(1-methyl-1H-tetrazol-5-yl)thiomethyl-3-cephem-4-carboxylic acid (syn isomer, 1.50 g.).

I.R. $\nu_{max}^{Nujol}$: 3340, 3200, 1770, 1665, 1600 cm$^{-1}$.

N.M.R. $\delta$(DMSO-d$_6$, ppm): 3.30–3.88 (4H, m), 3.93 (3H, s), 3.88–4.60 (4H, m), 5.05 (1H, d, J=5.0 Hz), 5.68 (1H, d,d, J=5.0 Hz, 8.0 Hz), 6.74 (1H, s), 7.26 (2H, broad s), 9.47 (1H, d, J=8.0 Hz).

EXAMPLE 8

(1) 2-(2-Formamidothiazol-4-yl)-2-(2-formyloxyethoxyimino)acetic acid (syn isomer 2.9 g.), N,N-dimethylformamide (0.8 g.), phosphoryl chloride (1.7 g.) and dry ethyl acetate (23 ml.) were treated in a similar manner to that of the Example 1-(1) to give an activated acid solution. The solution was added to a solution of 7-amino-3-methyl-3-cephem-4-carboxylic acid (2.0 g.) and trimethylsilylacetamide (8.6 g.) in dry ethyl acetate (40 ml.) at −10° C. and stirred at the same temperature for an hour. After adding water (30 ml.) to the reaction mixture, the organic layer was separated and extracted with an aqueous solution of sodium bicarbonate (30 ml.). The extract was adjusted to pH 2.5 with conc. hydrochloric acid and extracted with ethyl acetate (50 ml.). The extract was washed with a saturated aqueous solution of sodium chloride, dried and evaporated in vacuo. The residue was triturated with diisopropyl ether to give 7-[2-(2-formamidothiazol-4-yl)-2-(2-formyloxyethoxyimino)acetamido]-3-methyl-3-cephem-4-carboxylic acid (syn isomer, 2.10 g.).

I.R. $\nu_{max}^{Nujol}$: 3150, 1765, 1675 cm$^{-1}$.

N.M.R. $\delta$(DMSO-d$_6$, ppm): 2.03 (3H, s), 3.45 (2H, q, J=18 Hz), 4.36 (4H, m), 5.11 (1H, d, J=5 Hz), 5.75 (1H, d,d, J=5 Hz, 8 Hz), 7.46 (1H, s), 8.24 (1H, s), 8.53 (1H, s), 9.63 (1H, d, J=8 Hz).

(2) A mixture of 7-[2-(2-formamidothiazol-4-yl)-2-(2-formyloxyethoxyimino)acetamido]-3-methyl-3-cephem-4-carboxylic acid (syn isomer, 2.0 g.), conc. hydrochloric acid (1.35 g.), methanol (20 ml.) and tetrahydrofuran (20 ml.) was stirred at room temperature for 6 hours. After evaporating the reaction mixture in vacuo, the residue was subjected to column chromatography on non-ionic adsoption resin "Diaion HP-20" (trademark, manufactured by Mitsubishi Chemical Industries Ltd.) and eluted with 20% isopropyl alcohol. The eluate was concentrated in vacuo to give 7-[2-(2-aminothiazol-4-yl)-2-(2-hydroxyethoxyimino)acetamido]-3-methyl-3-cephem-4-carboxylic acid (syn isomer, 0.8 g.).

I.R. $\nu_{max}^{Nujol}$: 3350, 3200, 1765, 1660 cm$^{-1}$.

N.M.R. $\delta$(DMSO-d$_6$, ppm): 2.00 (3H, s), 3.41 (2H, m), 3.50–3.93 (2H, m), 3.93–4.40 (2H, m), 5.18 (1H, d, J=5.0

Hz), 5.69 (1H, d,d, J=5.0 Hz, 8.0 Hz), 6.79 (1H, s), 9.47 (1H, d, J=8.0 Hz).

EXAMPLE 9

(1) A solution of phosphoryl chloride (3.68 g.), N,N-dimethylformamide (1.75 g.) and tetrahydrofuran (4 ml.) was stirred at −5° to −10° C. for 30 minutes and added to a suspension of 2-(2-formamidothiazol-4-yl)-2-carbamoylmethoxyiminoacetic acid (syn isomer, 2 g.) in tetrahydrofuran (16 ml.). The mixture was stirred at the same temperature to give an activated acid solution. On the other hand, a suspension of 7-amino-3-(1-methyl-1H-tetrazol-5-yl)thiomethyl-3-cephem-4-carboxylic acid (3.62 g.) in 50% aqueous acetone (36 ml.) was adjusted to pH 7.5 with triethylamine. The activated acid solution was added dropwise to the above solution at 0° to −5° C. while keeping at pH 7.5 to 8.0 with triethylamine and stirred at the same temperature for 30 minutes. Ethyl acetate (100 ml.) was added to the resultant solution and adjusted to pH 2.5 with 10% hydrochloric acid. After filtration, the filtrate was extracted with ethyl acetate (100 ml.) twice. The extracts were washed with a saturated aqueous solution of sodium chloride, dried over magnesium sulfate and concentrated in vacuo. The residue was triturated with diethyl ether and the precipitates were collected by filtration to give 7-[2-(2-formamidothiazol-4-yl)-2-cyanomethoxyiminoacetamido]-3-(1-methyl-1H-tetrazol-5-yl)thiomethyl-3-cephem-4-carboxylic acid (syn isomer, 2.12 g.).

I.R. $\nu_{max}^{Nujol}$: 3210 (broad), 1780, 1680, 1545 cm$^{-1}$.

N.M.R. δ(DMSO-d$_6$, ppm): 3.74 (2H, s), 3.97 (3H, s), 4.34 (2H, s), 5.08 (2H, s), 5.17 (1H, d, J=5 Hz), 5.82 (1H, d,d, J=5 Hz, 8 Hz), 7.53 (1H, s), 8.53 (1H, s), 9.87 (1H, d, J=8 Hz), 12.77 (1H, broad s).

(2) A solution of 7-[2-(2-formamidothiazol-4-yl)-2-cyanomethoxyiminoacetamido]-3-(1-methyl-1H-tetrazol-5-yl)thiomethyl-3-cephem-4-carboxylic acid (syn isomer, 2.05 g.) and conc. hydrochloric acid (1.52 g.) in methanol (30 ml.) and tetrahydrofuran (20 ml.) was stirred at room temperature for 2 hours. After the solvent was evaporated in vacuo, the residue was dissolved in 10% aqueous solution of sodium hydroxide. After filtration, the filtrate was adjusted to pH 3.0 with 10% hydrochloric acid and stirred under ice-cooling for 30 minutes. The precipitates were collected by filtration, washed with water and dried to give 7-[2-(2-aminothiazol-4-yl)-2-cyanomethoxyiminoacetamido]-3-(1-methyl-1H-tetrazol-5-yl)thiomethyl-3-cephem-4-carboxylic acid (syn isomer, 1.25 g.).

I.R. $\nu_{max}^{Nujol}$: 3350, 3230. 3130, 1775, 1680, 1630 cm$^{-1}$.

N.M.R. δ(DMSO-d$_6$, ppm): 3.72 (2H, s), 3.96 (3H, s), 4.34 (2H, s), 5.03 (2H, s), 5.17 (1H, d, J=5 Hz), 5.80 (1H, d, d, J=5 Hz, 8 Hz), 6.90 (1H, s), 7.32 (2H, broad s), 9.82 (1H, d, J=8 Hz).

EXAMPLE 10

(1) A solution of 2-(2-formamidothiazol-4-yl)-2-carbamoylmethoxyiminoacetic acid (syn isomer, 1.5 g.), N,N-dimethylformamide (1.31 g.) and phosphoryl chloride (2.74 g.) in tetrahydrofuran (15 ml.) and a solution of 7-amino-3-(1-allyl-1H-tetrazol-5-yl)thiomethyl-3-cephem-4-carboxylic acid (2.96 g.) in 50% aqueous acetone (30 ml.) were treated in a similar manner to that of Example 9-(1) to give 7-[2-(2-formamidothiazol-4-yl)-2-cyanomethoxyiminoacetamido]-3-(1-allyl-1H-tetrazol-5-yl)thiomethyl-3-cephem-4-carboxylic acid (syn isomer, 2.22 g.).

I.R. $\nu_{max}^{Nujol}$: 3200 (broad), 1780, 1680 1540 cm$^{-1}$.

N.M.R. δ(DMSO-d$_6$, ppm): 3.74 (2H, q, J=20 Hz), 4.38 (2H, q, J=14 Hz), 4.7–6.8 (9H, m), 7.56 (1H, s), 8.53 (1H, s), 9.92 (1H, d, J=8 Hz), 12.66 (1H, broad s).

(2) A solution of 7-[2-(2-formamidothiazol-4-yl)-2-cyanomethoxyiminoacetamido]-3-(1-allyl-1H-tetrazol-5-yl)thiomethyl-3-cephem-4-carboxylic acid (syn isomer, 2.1 g.) and conc. hydrochloric acid (1.6 g.) in methanol 21 ml.) and tetrahydrofuran (5 ml.) was treated in a similar manner to that of Example 9-(2) to give 7-[2-(2-aminothiazol-4-yl)-2-cyanomethoxyiminoacetamido]-3-(1-allyl-1H-tetrazol-5-yl)thiomethyl-3-cephem-4-carboxylic acid (syn isomer, 1.40 g.).

I.R. $\nu_{max}^{Nujol}$: 3350, 3230, 1780, 1680, 1630, 1540 cm$^{-1}$.

N.M.R. δ(DMSO-d$_6$, ppm): 3.70 (2H, s), 4.38 (2H, q, J=14 Hz), 4.2–6.8 (9H, m), 6.88 (1H, s), 7.31 (2H, broad s), 9.77 (1H, d, J=8 Hz).

EXAMPLE 11

(1) A solution of 2-(2-formamidothiazol-4-yl)-2-carbamoylmethoxyiminoacetic acid (syn isomer, 1.35 g.), N,N-dimethylformamide (0.814 g.) and phosphoryl chloride (1.71 g.) in tetrahydrofuran (13.4 ml.) and a solution of 7-amino-3-(1-n-hexyl-1H-tetrazol-5-yl)thiomethyl-3-cephem-4-carboxylic acid (1.95 g.) in 50% aqueous acetone (20 ml.) were treated in a similar manner to that of Example 9-(1) to give 7-[2-(2-formamidothiazol-4-yl)-2-cyanomethoxyiminoacetamido]-3-(1-n-hexyl-1H-tetrazol-5-yl)thiomethyl-3-cephem-4-carboxylic acid (syn isomer, 1.2 g.).

I.R. $\nu_{max}^{Nujol}$: 3180 (broad), 1770, 1665, 1540 cm$^{-1}$.

N.M.R. δ(DMSO-d$_6$, ppm): 0.88 (3H, t, J=5 Hz), 1.0–2.2 (8H, m), 3.80 (2H, s), 4.0–4.9 (4H, m), 5.14 (2H, s), 5.23 (1H, d, J=5 Hz), 5.88 (1H, d, d, J=5 Hz, 8 Hz), 7.58 (1H, s), 8.58 (1H, s), 9.93 (1H, d, J=8 Hz), 12.81 (1H, broad s).

(2) A solution of 7-[2-(2-formamidothiazol-4-yl)-2-cyanomethoxyiminoacetamido]-3-(1-n-hexyl-1H-tetrazol-5-yl)thiomethyl-3-cephem-4-carboxylic acid (syn isomer, 1.11 g.) and conc. hydrochloric acid (0.73 g.) in methanol (11 ml.) and tetrahydrofuran (5 ml.) was treated in a similar manner to that of Example 9-(2) to give 7-[2-(2-aminothiazol-4-yl)-2-cyanomethoxyiminoacetamido]-3-(1-n-hexyl-1H-tetrazol-5-yl)thiomethyl-3-cephem-4-carboxylic acid (syn isomer, 0.75 g.).

I.R. $\nu_{max}^{Nujol}$: 3360, 3230, 1780, 1680, 1630 cm$^{-1}$.

N.M.R. δ(DMSO-d$_6$, ppm): 0.87 (3H, t, J=5 Hz), 0.9–2.2 (8H, m), 3.73 (2H, s), 4.0–4.8 (4H, m), 5.03 (2H, s), 5.16 (1H, d, J=5 Hz), 5.80 (1H, d,d, J=5 Hz, 8 Hz), 6.92 (1H, s), 7.33 (2H, broad s), 9.81 (1H, d, J=8 Hz).

EXAMPLE 12

(1) 2-(2-Formamidothiazol-4-yl)-2-(2-formyloxyethoxyimino)acetic acid (syn isomer, 3.6 g.) was added to Vilsmeier reagent prepared from N,N-dimethylformamide (1.1 g.) and phosphoryl chloride (2.3 g.) in dry ethyl acetate (48.4 ml.) at 0° to 5° C. and stirred for 30 minutes to give an activated acid solution. The solution was added to a solution of 7-amino-3-(1-allyl-1H-tetrazol-5-yl)thiomethyl-3-cephem-4-carboxylic acid (4.4 g.) and trimethylsilylacetamide (11.4 g.) in ethyl acetate (88 ml.) at −10° C. and stirred at −10° to −5° C. for 1.5 hours. After adding water (100 ml.) to the resultant solution, the solution was adjusted to pH 7.0 with a saturated aqueous solution of sodium bicarbonate. The aqueous layer was separated washed with ethyl acetate and diethyl ether in turn and acidified to pH 2.5 with conc. hydrochloric acid. The precipitates were collected by filtration, washed with water and dried over phosphorus pentoxide to give 7-[2-(2-formamidothiazol-4-yl)-2-(2-formyloxyethoxyimino)acetamido]-3-(1-allyl-1H-tetrazol-5-yl)thiomethyl-3-cephem-4-carboxylic acid (syn isomer, 5.22 g.)

I.R. $\nu_{max}^{Nujol}$: 3265, 1780, 1720, 1680 cm$^{-1}$.

N.M.R. $\delta$(DMSO-d$_6$, ppm): 3.74 (2H, m), 4.13–4.70 (6H, m), 4.85–5.53 (5H, m), 5.70–6.42 (2H, m), 7.48 (1H, s), 8.26 (1H, s), 3.56 (1H, s), 9.69 (1H, d, J=9 Hz).

(2) A solution of 7-[2-(2-formamidothiazol-4-yl)-2-(2-formyloxyethoxyimino)acetamido]-3-(1-allyl-1H-tetrazol-5-yl)thiomethyl-3-cephem-4-carboxylic acid (syn isomer, 5.0 g.) and conc. hydrochloric acid (3.34 g.) in methanol (35 ml.) and tetrahydrofuran (5 ml.) was treated in a similar manner to that of Example 2-(2) to give 7-[2-(2-aminothiazol-4-yl)-2-(2-hydroxyethoxyimino)acetamido]-3-(1-allyl-1H-tetrazol-5-yl)thiomethyl-3-cephem-4-carboxylic acid hydrochloride (syn isomer, 4.73 g.).

I.R. $\nu_{max}^{Nujol}$: 3420, 3300, 3100, 1790, 1170, 1725, 1678, 1660, 1640 cm$^{-1}$.

N.M.R. $\delta$(DMSO-d$_6$, ppm): 3.37–4.00 (4H, m), 4.00–4.68 (4H, m), 4.80–5.50 (5H, m), 5.58–6.33 (2H, m), 6.97 (1H, s), 7.11 (2H, broad s), 9.75 (1H, d, J=8 Hz).

EXAMPLE 13

2-(2-Aminothiazol-4-yl)-2-cyanomethoxyiminoacetic acid (syn isomer, 2.0 g.), phosphoryl chloride (3.2 g.), N,N-dimethylformamide (0.77 g.), trimethylsilylacetamide (1.87 g.) and ethyl acetate (30 ml.) were treated in a similar manner to that of Example 1 to give an activated acid solution. The solution was added to a solution of 7-aminocephalosporanic acid (2.4 g.) and trimethylsilylacetamide (9.2 g.) in ethyl acetate (30 ml.) and the mixture was treated in a similar manner to that of Example 1 to give 7-[2-(2-aminothiazol-4-yl)-2-cyanomethoxyiminoacetamido]-cephalosporanic acid (syn isomer, 1.1 g.).

I.R. $\nu_{max}^{Nujol}$: 3400–3200, 1760, 1720, 1670, 1600, 1530 cm$^{-1}$.

N.M.R. $\delta$(DMSO-d$_6$, ppm): 2.00 (2H, s), 3.40 (2H, broad s), 4.88 (2H, q, J=13 Hz), 5.00 (2H, s), 5.07 (1H, d, J=5 Hz), 5.65 (1H, dd, J=5 Hz, 8 Hz), 6.88 (1H, s), 9.73 (1H, d, J=8 Hz).

EXAMPLE 14

Phosphoryl chloride (1.7 g.) was added to a stirred suspension of 2-(2-aminothiazol-4-yl)-2-(2,2,2-trifluoroethoxyimino)acetic acid (syn isomer, 2.4 g.) in tetrahydrofuran (20 ml.) and water (0.15 g.) at 2° C., and stirred at 2° to 5° C. for 30 minutes. Trimethylsilylacetamide (2.0 g.) was added to the solution and stirred at the same temperature for 20 minutes. Phosphoryl chloride (1.7 g.) was added to the solution and stirred for 15 minutes. After adding N,N-dimethylformamide (0.81 g.) to the solution, the solution was stirred at 3° to 6° C. for an hour. Thus obtained solution was added to a solution of 7-aminocephalosporanic acid (2.42 g.), trimethylsilylacetamide (8.4 g.) in ethyl acetate (30 ml.) at −30° C. all at once, and stirred at the same temperature for an hour. Water (50 ml.) was added to the resultant solution at −10° C., adjusted to pH 7.0 with saturated aqueous solution, of sodium bicarbonate and the aqueous layer was separated. The remaining organic solvent was evaporated from the aqueous solution in vacuo. The solution was adjusted to pH 4.3 with 10% hydrochloric acid under ice-cooling, and subjected to column chromatography on macroporous non-ionic adsorption resin "Diaion HP-20" (trademark: manufactured by Mitsubishi Chemical Industries Ltd.) and eluted with 30% aqueous acetone. The eluate was concentrated in vacuo and lyophilized to give 7-[2-(2-aminothiazol-4-yl)-2-(2,2,2-trifluoroethoxyimino)acetamido]cephalosporanic acid (syn isomer, 1.55 g.).

I.R. $\nu_{max}^{Nujol}$: 3400–3200, 1780, 1740, 1680, 1630, 1540 cm$^{-1}$.

N.M.R. $\delta$(DMSO-d$_6$, ppm): 2.00 (3H, s), 3.68 (2H, broad s), 4.65 (2H, q, J=8 Hz), 4.82 (2H, q, J=12 Hz), 5.13 (1H, d, J=5 Hz), 5.76 (1H, dd, J=5 Hz, 8 Hz), 6.80 (1H, s), 7.28 (2H, broad s), 9.70 (1H, d, J=8 Hz).

EXAMPLE 15

A solution of 2-(2-aminothiazol-4-yl)-2-(2-chloroethoxyimino)acetic acid (syn isomer, 2.0 g.), phosphoryl chloride (2.7 g.), N,N-dimethylformamide (0.766 g.) and trimethylsilylacetamide (1.25 g.) in a mixture of water (109 mg.) and tetrahydrofuran (20 ml.), and a solution of 7-aminocephalosporanic acid (2.3 g.), trimethylsilylacetamide (7.7 g.) and ethyl acetate (23 ml.) were treated in a similar manner to that of Example 14, and the resultant solution was subjected to column chromatography on macroporous nonionic, adsorption resin "Diaion HP-20" (trademark: manufactured by Mitsubishi Chemical Industries Ltd.) and eluted with 20% aqueous isopropyl alcohol. The eluate was concentrated in vacuo and lyophilized to give sodium 7-[2-(2-aminothiazol-4-yl)-2-(2-chloroethoxyimino)acetamido]cephalosporanate (syn isomer, 0.77 g.).

I.R. $\nu_{max}^{Nujol}$: 3350, 3200, 1770, 1670, 1540 cm$^{-1}$.

N.M.R. $\delta$(DMSO-d$_6$, ppm): 2.03 (3H, s), 3.42 (2H, q, J=18 Hz), 3.83 (2H, t, J=6 Hz), 4.32 (2H, t, J=6 Hz), 4.95 (2H, q, J=13 Hz), 5.06 (1H, d, J=5 Hz), 5.65 (1H, dd, J=5 Hz, 8 Hz), 6.82 (1H, s), 7.31 (2H, broad s), 9.52 (1H, d, J=8 Hz).

EXAMPLE 16

(1) A solution of 2-(2-formamidothiazol-4-yl)-2-(2-bromoethoxyimino)acetic acid (syn isomer, 1 g.), N,N-dimethylformamide (0.272 g.) and phosphoryl chloride (0.572 g.) in tetrahydrofuran (10 ml.), and a solution of 7-amino-3-(1,3,4-thiadiazol-2-yl)-thiomethyl-3-cephem-4-carboxylic acid (1.44 g.) in 50% aqueous acetone (22 ml.) were treated in a similar manner to that of Example 9 (1) to give 7-[2-(2-formamidothiazol-4-yl)-2-(2-bromoethoxyimino)acetamido]-3-(1,3,4-thiadiazol-2-yl)thiomethyl-3-cephem-4-carboxylic acid (syn isomer, 1.57 g.).

I.R. $\nu_{max}^{Nujol}$: 3180 (shoulder), 1770, 1670, 1540 cm$^{-1}$.

N.M.R. $\delta$(DMSO-d$_6$, ppm): 3.3–3.9 (4H, m), 4.1–4.8 (4H, m), 5.23 (1H, d, J=5Hz), 5.84 (1H, dd, J=5 Hz, 9 Hz), 7.63 (1H, s), 8.72 (1H, s), 9.57 (1H, s), 9.71 (1H, d, J=9 Hz), 12.71 (1H, broad s). (2) A mixture of 7-[2-(2-formamidothiazol-4-yl)-2-(2-bromoethoxyimino)acetamido]-3-(1,3,4-thiadiazol-2-yl)thiomethyl-3-cephem-4-carboxylic acid (syn isomer, 1.5 g.), conc. hydrochloric acid (0.99 g.), tetrahydrofuran (10 ml.) and methanol (22 ml.) was treated in similar manner to that of Example 9 (2), to give 7-[2-(2-aminothiazol-4-yl)-2-(2-bromoethoxyimino)acetamido]-3-(1,3,4-thiadiazol- 2-yl)thiomethyl-3-cephem-4-carboxylic acid (syn isomer, 1.15 g.).

I.R. $\nu_{max}^{Nujol}$: 3340 (broad), 1770, 1670, 1530 cm$^{-1}$.

N.M.R. δ(DMSO-d$_6$, ppm): 3.3–4.1 (4H, m), 4.1–4.8 (4H, m), 5.18 (1H, d, J=5 Hz), 5.84 (1H, dd, J=5 Hz, 8 Hz), 6.84 (1H, s), 7.27 (2H, broad s), 9.58 (1H, s), 9.60 (1H, d, J=8 Hz).

EXAMPLE 17

(1) Vilsmeier reagent prepared from N,N-dimethyl formamide (0.2 g.) and phosphoryl chloride (0.42 g.) in a conventional manner was added to ethyl acetate (10 ml.), and then 2-(2-formamidothiazol-4-yl)-2-(2,2,2-trifluoroethoxyimino)acetic acid (syn isomer, 0.75 g.) was added to the solution under ice-cooling and stirred at the same temperature for 30 minutes. The solution was added to a solution of 7-amino-3-(1,3,4-thiadiazol-2-yl)thiomethyl-3-cephem-4-carboxylic acid (0.83 g.) and trimethylsilylacetamide (2.62 g.) in ethyl acetate (30 ml.) at −30° C., and stirred at the same temperature for 1.5 hours. After adding ethyl acetate (100 ml.) and water to the resultant solution, the ethyl acetate layer was separated. Water (100 ml.) was added to the ethyl acetate solution adjusted to pH 7.5 with saturated aqueous solution of sodium bicarbonate. The aqueous layer was separated and the ethyl acetate (150 ml.) was added thereto, and adjusted to pH 1.5 with hydrochloric acid. The ethyl acetate layer was separated, washed with saturated aqueous solution of sodium chloride, dried over magnesium sulfate, and concentrated in vacuo. The residue was triturated with diethyl ether to give 7-[2-(2-formamidothiazol-4-yl)-2-(2,2,2-trifluoroethyoxyimino)acetamido]-3-(1,3,4-thiadiazol-2-yl)thiomethyl-3-cephem-4-carboxylic acid (syn isomer, 1.2 g.).

I.R. $\nu_{max}^{Nujol}$: 3300–3150, 1780, 1690, 1680, 1540 cm$^{-1}$.

N.M.R. δ(DMSO-d$_6$, ppm): 3.58 (2H, broad s), 4.47 (2H, q, J=14 Hz), 4.77 (2H, q, J=8.5 Hz), 5.20 (1H, d, J=5 Hz), 5.87 (1H, dd, J=5 Hz, 8 Hz), 7.53 (1H, s), 8.55 (1H, s), 9.57 (1H, s), 9.87 (1H, d, J=8 Hz), 12.7 (1H, broad s).

(2) A mixture of 7-[2-(2-formamidothiazol-4-yl)-2-(2,2,2-trifluoroethoxyimino)acetamido]-3-(1,3,4-thiadiazol-2-yl)thiomethyl-3-cephem-4-carboxylic acid (syn isomer, 1.1 g.), conc. hydrochloric acid (0.56 g.) and methanol (22 ml.) was stirred at room temperature for 3 hours. After removing the solvent from the resultant mixture in vacuo, water (15 ml.) was added to the residue and adjusted to pH 7.5 with saturated aqueous solution of sodium bicarbonate. The solution was treated with activated charcoal and adjusted to pH 3 with 10% hydrochloric acid. The precipitates were collected by filtration, washed with water and dried to give 7-[2-(2-aminothiazol-4-yl)-2-(2,2,2-trifluoroethoxyimino)acetamido]-3-(1,3,4-thiadiazol-2-yl)thiomethyl-3-cephem-4-carboxylic acid (syn isomer, 0.75 g.).

I.R. $\nu_{max}^{Nujol}$: 3400–3200, 1780, 1680, 1630, 1530 cm$^{-1}$.

N.M.R. δ(DMSO-d$_6$, ppm): 3.71 (2H, q, J=17 Hz), 4.46 (2H, q, J=13 Hz), 4.72 (2H, q, J=8.5 Hz), 5.18 (1H, d, J=5 Hz), 5.80 (1H, dd, J=5 Hz, 8 Hz), 6.88 (1H, s), 9.58 (1H, s), 9.81 (1H, d, J=8 Hz).

EXAMPLE 18

(1) A solution of 2-(2-formamidothiazol-4-yl)-2-(2,2,2-trifluoroethoxyimino)acetic acid (syn isomer, 1.78 g.), N,N-dimethylformamide (0.48 g.) and phosphoryl chloride (1.01 g.) in ethyl acetate (18 ml.), and a solution of 7-amino-3-(1-methyl-1H-tetrazol-5-yl)thiomethyl-3-cephem-4-carboxylic acid (1.97 g.) and trimethylsilylacetamide (4.72 g.) in ethyl acetate (28 ml.). were treated in a similar manner to that of Example 17 (1) to give 7-[2-(2-formamidothiazol-4-yl)-2-(2,2,2-trifluoroethoxyimino)acetamido]-3-(1-methyl-1H-tetrazol-5-yl)thiomethyl-3-cephem-4-carboxylic acid (syn isomer, 1.05 g.).

I.R. $\nu_{max}^{Nujol}$: 3200, 1770, 1670, 1530 cm$^{-1}$.

N.M.R. δ(DMSO-d$_6$, ppm): 3.70 (2H, broad s), 3.92 (3H, s), 4.30 (2H, broad s), 4.75 (2H, q, J=9 Hz), 5.17 (1H, d, J=5 Hz), 5.83 (1H, dd, J=5 Hz, 8 Hz), 7.50 (1H, s), 8.55 (1H, s), 9.83 (1H, d, J=8 Hz), 12.7 (1H, broad s).

(2) A mixture of 7-[2-(2-formamidothiazol-4-yl)-2-(2,2,2-trifluoroethoxyimino)acetamido]-3-(1-methyl-1H-tetrazol-5-yl)thiomethyl-3-cephem-4-carboxylic acid (syn isomer, 1.0 g.) conc. hydrochloric acid (0.33 g.) and methanol (10 ml.) was stirred at room temperature for 4 hours. The precipitates were collected by filtration and washed with diethyl ether to give 7-[2-(2-aminothiazol-4-yl)-2-(2,2,2-trifluoroethoxyimino)acetamido]-3-(1-methyl-1H-tetrazol-5-yl)thiomethyl-3-cephem-4-carboxylic acid hydrochloride (syn isomer, 0.6 g.).

I.R. $\nu_{max}^{Nujol}$: 3340, 1770, 1710, 1660, 1560 cm$^{-1}$.

N.M.R. δ(DMSO-d$_6$, ppm): 3.70 (2H, broad s), 3.92 (3H, s), 4.30 (2H, broad s), 4.78 (2H, q, J=9 Hz), 5.15 (1H, d, J=5 Hz), 5.78 (1H, dd, J=5 Hz), 8 Hz), 7.03 (1H, s), 9.93 (1H, d, J=8 Hz).

EXAMPLE 19

(1) A solution of 2-(2-formamidothiazol-4-yl)-2-(2,2,2-trifluoroethoxyimino)acetic acid (syn isomer, 1.5 g.), N,N-dimethylformamide (0.40 g.) and phosphoryl chloride (0.84 g.) in ethyl acetate (15 ml.) and a solution of 7-amino-3-(1-allyl-1H-tetrazol-5-yl)thiomethyl-3-cephem-4-carboxylic acid (1.77 g.) and trimethylsilylacetamide (3.93 g.) in ethyl acetate (25 ml.) were treated in a similar manner to that of Example 17 (1) to give 7-[2-(2-formamidothiazol-4-yl)-2-(2,2,2-trifluoroethoxyimino)acetamido]-3-(1-allyl-1H-tetrazol-5-yl)thiomethyl-3-cephem-4-carboxylic acid (syn isomer, 1.25 g.).

I.R. $\nu_{max}^{Nujol}$: 3200, 1760, 1670, 1590, 1540 cm$^{-1}$.

N.M.R. δ(DMSO-d$_6$, ppm): 3.67 (2H, broad s), 4.86–4.00 (4H-m), 5.42–4.98 85H, m), 6.36–5.73 (1H, m), 7.53 (1H, s), 8.58 (1H, s), 9.82 (1H, d, J=8 Hz).

(2) A mixture of 7-[2-(2-formamidothiazol-4-yl)-2-(2,2,2-trifluoroethoxyimino)acetamido]-3-(1-allyl-1H-tetrazol-5-yl)thiomethyl-3-cephem-4-carboxylic acid (syn isomer, 1.2 g.), conc. hydrochloric acid (0.4 g.) and methanol (13 ml.) was treated in a similar manner to that of Example 17 (2) to give 7-[2-(2-aminothiazol-4-yl)-2-(2,2,2-trifluoroethoxyimino)acetamido]-3-(1-allyl-1H-tetrazol-5-yl)thiomethyl-3-cephem-4-carboxylic acid (syn isomer, 0.55 g.).

I.R. $\nu_{max}^{Nujol}$: 3350, 1770, 1670, 1620, 1530 cm$^{-1}$.

N.M.R. δ(DMSO-d$_6$, ppm): 3.70 (2H, broad s). 4.37 (2H, q, J=13 Hz), 4.68 (2H, q, J=8 Hz), 5.4–4.97 (5H, m), 6.33–5.7 (2H, m), 6.83 (1H, s), 7.28 (2H, broad s), 9.73 (1H, d, J=8 Hz).

EXAMPLE 20

(1) Vilsmeier reagent was prepared from N,N-dimethylformamide (0.45 g.) and phosphoryl chloride (1.03 g.) in a usual manner. 2-(2-Formamidothiazol-4-yl)-2-(2-tert-butoxycarbonylaminoethoxyimino)acetic acid (syn isomer, 2.0 g.) was added to the stirred suspension of the Vilsmeier reagent in ethyl acetate (40 ml.) under ice cooling and stirred at the same temperature for 30 minutes [Solution A]. Trimethylsilylacetamide (5.9 g.) was added to a stirred suspension of 7-amino-3-(1-methyl-1H-tetrazol-5-yl)thiomethyl-3-cephem-4-carboxylic acid (1.8 g.) in ethyl acetate (30 ml.), and the mixture was stirred at the room temperature for 30 minutes. To the solution was added the solution A all at once at −30° C., and the resultant solution was stirred at −10° to −40° C. for an hour. Water and ethyl acetate (100 ml.) were added to reaction mixture at −10° C. and, the ethyl acetate layer was separated. Water (100 ml.) was added to the ethyl acetate solution, and adjusted to pH 7.0 with a saturated sodium bicarbonate aqueous solution. After the aqueous layer was separated, ethyl acetate was added thereto. The mixture was adjusted to pH 3.0 with 10% hydrochloric acid under ice-cooling. The ethyl acetate layer was washed with a saturated sodium chloride aqueous solution, dried over magnesium sulfate and evaporated in vacuo. The residue was pulverized with diisopropyl ether, collected by filtration to give 7-[2-(2-formamidothiazol-4-yl)-2-(2-tert-butoxycarbonylaminoethoxyimino)acetamido]-3-(1-methyl-1H-tetrazol-5-yl)thiomethyl-3-cephem-4-carboxylic acid (syn isomer, 2.8 g.).

I.R. $\nu_{max}^{Nujol}$: 3250, 1780, 1690, 1540 cm$^{-1}$.

N.M.R. $\delta$(DMSO-d$_6$, ppm): 1.35 (9H, s), 3.33 (2H, m), 3.70 (2H, m), 3.95 (3H, s), 4.17 (2H, m), 4.32 (2H, m), 5.18 (1H, d, J=5 Hz), 5.88 (1H, d.d, J=8 Hz, 5 Hz), 7.43 (1H, s), 8.52 (1H, s), 9.60 (1H, d, J=8 Hz), 12.55 (1H, broad s)

(2) A solution of 7-[2-(2-formamidothiazol-4-yl)-2-(2-tert-butoxycarbonylaminoethoxyimino)acetamido]-3-(1-methyl-1H-tetrazol-5-yl)thiomethyl-3-cephem-4-carboxylic acid (syn isomer, 2.6 g.), conc. hydrochloric acid (2 g.) and methanol (40 ml.) was stirred at room temperature for 3 hours. After evaporating the solvent in vacuo, methanol was added to the residue and mixture was evaporated in vacuo again. The residue was dissolved in water (30 ml.) and adjusted to pH 3.5 with a saturated sodium bicarbonate aqueous solution under ice-cooling. The solution was subjected to column chromatography on macroporous non-ionic adsorption resin "Diaion HP-20" [trademark, manufactured by Mitsubishi Chemical Industries Ltd.], and eluted with 30% aqueous isopropyl alcohol. The eluate was concentrated in vacuo and the residue was lyophilized to give 7-[2-(2-aminothiazol-4-yl)-2-(2-aminoethoxymino)acetamido]-3-(1-methyl-1H-tetrazol-5-yl)thiomethyl-3-cephem-4-carboxylic acid (syn isomer, 0.7 g.)

I.R. $\nu_{max}^{Nujol}$: 3300, 3150, 1770, 1660, 1620, 1530 cm$^{-1}$.

N.M.R. $\delta$(DMSO-d$_6$, ppm): 3.18 (2H, m), 3.55 (2H, m), 3.90 (3H, s), 4.28 (4H, m), 5.00 (1H, d, J=5 Hz), 5.70 (1H, d.d, J=8 Hz, 5 Hz), 6.80 (1H, s), 9.50 (1H, m).

EXAMPLE 21

(1) Vilsmeier reagent was prepared from N,N-dimethylformamide (0.45 g.) and phosphoryl chloride (1.03 g.) in a usual manner. 2-(2-Formamidothiazol-4-yl)-2-(2-tert-butoxycarbonylaminoethoxyiminoacetic acid (syn isomer, 2 g.) was added to a stirred suspension of the Vilsmeier reagent in ethyl acetate (20 ml.) under ice-cooling and stirred at the same temperature for 30 minutes [Solution A]. Sodium bicarbonate (1.9 g.) was added to a stirred suspension of 7-amino-3-carbamoyloxymethyl-3-cephem-4-carboxylic acid (1.5 g.) in water (20 ml.) and acetone (20 ml.). The solution A was added dropwise to the solution at pH 7.5 to 8.5 and stirred at 0° to 5° C. for an hour. The aqueous layer was separated, washed with ethyl acetate and adjusted to pH 3.0 with 10% hydrochloric acid. The precipitates were collected by filtration, washed with water and dried over phosphorus pentoxide to give 7-[2-(2-formamidothiazol-4-yl)-2(2-tert-butoxycarbonylaminoethoxyimino)acetamido]-3-carbamoyloxymethyl-3-cephem-4-carboxylic acid (syn isomer, 1.8 g.).

I.R. $\nu_{max}^{Nujol}$: 3350, 1775, 1680, 1550 cm$^{-1}$.

N.M.R. $\delta$(DMSO-d$_6$, ppm): 3.30 (2H, q, J=17 Hz), 3.55 (2H, m), 4.12 (2H, m), 4.78 (2H, q, J=13 Hz), 5.20 (1H, d, J=5 Hz), 5.87 (1H, d.d, J=8 Hz, 5 Hz), 7.43 (1H, s), 8.57 (1H, s), 9.55 (1H, d, J=8 Hz), 12.53 (1H, m).

(2) A solution of 7-[2-(2-formamidothiazol-4-yl)-2-(2-tert-butoxycarbonylaminoethoxyimino)acetamido]-3-carbamoyloxymethyl-3-cephem-4-carboxylic acid (syn isomer, 1.7 g.) and conc. hydrochloric acid (1.5 g.) in methanol (30 ml.) was stirred at room temperature for 3 hours. After evaporating the solvent in vacuo, methanol was added to the residue and then evaporated in vacuo again. The residue was dissolved in water (30 ml.) and adjusted to pH 3.5 with a sodium bicarbonate saturated aqueous solution under ice-cooling. The solution was subjected to column chromatography on macroporous non-ionic adsorption resin "Diaion HP-20" (trademark, manufactured by Mitsubishi Chemical Industries Ltd.) and eluted with 30% aqueous isopropyl alcohol. The eluate was concentrated in vacuo, and the residue was lyophilized to give 7-[2-(2-aminothiazol-4-yl)-2-(2-aminoethoxyimino)acetamido]-3-carbamoyloxymethyl-3-cephem-4-carboxylic acid (syn isomer, 1.1 g.).

I.R. $\nu_{max}^{Nujol}$: 3300, 3150, 1760, 1700, 1660, 1600 cm$^{-1}$.

N.M.R. $\delta$(DMSO-d$_6$, ppm): 3.33 (2H, m), 4.28 (4H, m), 4.75 (2H, m), 5.00 (1H, d, J=5 Hz), 5.63 (1H, d.d, J=8 Hz, 5 Hz), 6.78 (1H, s), 9.40 (1H, m).

EXAMPLE 22

(1) 2-(2-Formamidothiazol-4-yl)-2-(2-tert-butoxycarbonylaminoethoxyimino)acetic acid (syn isomer, 2 g.) and 7-amino-3-methyl-3-cephem-4-carboxylic acid (1.6 g.) were treated in a similar manner to that of Example 21-(1) to give 7-[2-(2-formamidothiazol-4-yl)-2-(2-tert-butoxycarbonylaminoethoxyimino)acetamido]-3-methyl-3-cephem-4-carboxylic acid (syn isomer, 2.1 g.).

I.R. $\nu_{max}^{Nujol}$: 3300, 1780, 1690, 1550 cm$^{-1}$.

N.M.R. $\delta$(DMSO-d$_6$, ppm): 1.37 (9H, s), 2.04 (3H, s), 3.45 (4H, m), 4.17 (2H, m), 5.22 (1H, d, J=5 Hz), 5.83 (1H, d.d, J=8 Hz, 5 Hz), 7.54 (1H, s), 8.67 (1H, s), 9.78 (1H, d, J=8 Hz).

(2) A mixture of 7-[2-(2-formamidothiazol-4-yl)-2-(2-tert-butoxycarbonylaminoethoxyimino)acetamido]-3-methyl-3-cephem-4-carboxylic acid (syn isomer, 1.9 g.), conc. hydrochloric acid (1.4 g.) and methanol (30 ml.) was treated in a similar manner to that of Example 21-(2) to give 7-[2-(2-aminothiazol-4-yl)-2-(2-aminoethoxyimino)acetamido]-3-methyl-3-cephem-4-carboxylic acid (syn isomer, 1.3 g.).

I.R. $\nu_{max}^{Nujol}$: 3300, 3150, 1750, 1650, 1610, 1570, 1530 cm$^{-1}$.

N.M.R. $\delta$(DMSO-d$_6$, ppm): 1.88 (3H, s), 3.23 (2H, m), 3.70 (2H, m), 4.32 (2H, m), 4.98 (1H, d, J=5 Hz), 5.62 (1H, d.d, J=8 Hz, 5Hz), 6.78 (1H, s), 9.50 (1H, m).

EXAMPLE 23

(1) 2-(2-Formamidothiazol-4-yl)-2-(3-tert-butoxycarbonylaminopropoxyimino)acetic acid (syn isomer, 1.86 g.) and 7-amino-3-(1-allyl-1H-tetrazol-5-yl)thiomethyl-3-cephem-4-carboxylic acid (1.77 g.) were treated in similar manner to that of Example 20-(1) to give 7-[2-(2-formamidothiazol-4-yl)-2-(3-tert-butoxycarbonylaminopropoxyimino)acetamido]-3-(1-allyl-1H-tetrazol-5-yl)thiomethyl-3-cephem-4-carboxylic acid (syn isomer, 1.2 g.).

I.R. $\nu_{max}^{Nujol}$: 3380, 3200, 1780, 1690, 1650, 1540 cm$^{-1}$.

N.M.R. $\delta$(DMSO-d$_6$, ppm): 1.38 (9H, s), 1.78 (2H, m), 3.05 (2H, m), 3.70 (2H, broad s), 4.13 (2H, t, J=7 Hz), 4.38 (2H, q, J=14 Hz), 4.80-5.45 (5H, m), 5.63-6.47 (2H, m), 7.45 (1H, s), 8.57 (1H, s), 9.68 (1H, d, J=8 Hz), 12.73 (1H, broad s).

(2) Conc. hydrochloric acid (0.5 ml.) was added to a solution of 7-[2-(2-formamidothiazol-4-yl)-2-(3-tert-butoxycarbonylaminopropoxyimino)acetamido]-3-(1-allyl-1H-tetrazol-5-yl)thiomethyl-3-cephem-4-carboxylic acid (syn isomer, 1.1 g.) in methanol (20 ml.) and stirred at room temperature for an hour. After evaporating the solvent in vacuo, methanol was added to the residue and evaporated again. The residue was dried over phosphorus pentoxide in vacuo to give 7-[2-(2-aminothiazol-4-yl)-2-(3-aminopropoxyimino)acetamido]-3-(1-allyl-1H-tetrazol-5-yl)thiomethyl-3-cephem-4-carboxylic acid dihydrochloride (syn isomer, 0.89 g.).

I.R. $\nu_{max}^{Nujol}$: 3500-3100, 1770, 1700, 1670, 1620, 1540 cm$^{-1}$.

N.M.R. $\delta$(DMSO-d$_6$, ppm): 2.07 (2H, m), 3.07 (2H, m), 3.77 (2H, broad s), 4.76-4.00 (4H, m), 5.50-4.83 (5H, m), 6.20-5.63 (2H, m), 7.00 (1H, s), 9.97 (1H, d, J=8 Hz).

EXAMPLE 24

(1) Vilsmeier reagent was prepared from dry N,N-dimethylformamide (0.3 g.) and phosphory chloride (0.5 g.) in dry ethyl acetate (1.2 ml.) in a usual manner. 2-(2-Formamidothiazol-4-yl)-2-(2-chloroethoxyimino)acetic acid (syn isomer, 0.9 g.) and dry ethyl acetate (10 ml.) were added to the mixture under ice-cooling and then stirred at the same temperature for 30 minutes. [Solution A]Trimethylsilylacetamide (2.9 g.) was added to a solution of 7-amino-3-(1-allyl-1H-tetrazol-5-yl)thiomethyl-3-cephem-4-carboxylic acid (1.0 g.) in dry ethyl acetate (20 ml.) and stirred at 40° C. for 30 minutes. To the solution was added the solution A at −10° C. and stirred at −5° to −10° C. for an hour. Water was added to the resultant solution and the organic layer was separated. Water was added to the organic layer and adjusted to pH 7.0 with sodium carbonate. The aqueous layer was separated, washed with ethyl acetate and adjusted to pH 4.5 with 10% hydrochloric acid. The solution was extracted with ethyl acetate. The extract was washed with a sodium chloride saturated aqueous solution, dried over magnesium sulfate and concentrated in vacuo. The residue was pulverized with diisopropyl ether. The precipitates were collected by filtration, washed with diisopropyl ether and dried to give 7-[2-(2-formamidothiazol-4-yl)-2-(2-chloroethoxyimino)acetamido]-3-(1-allyl-1H-tetrazol-5-yl)thiomethyl-3-cephem-4-carboxylic acid (syn isomer, 0.83 g.).

I.R. $\nu_{max}^{Nujol}$: 1770, 1670 cm$^{-1}$.

N.M.R. $\delta$(DMSO-d$_6$, ppm): 3.47-4.06 (4H, m), 4.06-4.70 (4H, m), 4.82-5.46 (5H, m), 5.65-6.41 (2H, m), 7.51 (1H, s), 8.57 (1H, s), 9.75 (1H, d, J=9 Hz).

(2) A suspension of 7-[2-(2-formamidothiazol-4-yl)-2-(2-chloroethoxyimino)acetamido]-3-(1-allyl-1H-tetrazol-5-yl)thiomethyl-3-cephem-4-carboxylic acid (syn isomer, 0.75 g.) and conc. hydrochloric acid (0.3 g.) in methanol (5.25 ml.) was stirred at 30° C. for 3 hours. After removing the solvent in vacuo, ethyl acetate and water were added to the residue and adjusted to pH 7.0 with sodium bicarbonate. The aqueous solution was separated, washed with ethyl acetate and adjusted to pH 3.0 with 10% hydrochloric acid. The ethyl acetate layer was separated, washed with a sodium chloride saturated aqueous solution, dried over magnesium sulfate and evaporated in vacuo. The residue was pulverized with diisopropyl ether. The precipitates were collected by filtration, washed with diisopropyl ether and dried to give 7-[2-(2-aminothiazol-4-yl)-2-(2-chloroethoxyimino)acetamido]-3-(1-allyl-1H-tetrazol-5-yl)thiomethyl-3-cephem-4-carboxylic acid (syn isomer, 0.43 g.).

I.R. $\nu_{max}^{Nujol}$: 3300, 1770, 1670, 1620 cm$^{-1}$.

N.M.R. $\delta$(DMSO-d$_6$, ppm): 3.50-3.97 (4H, m), 4.07-4.70 (4H, m), 4.79-5.50 (5H, m), 5.66-6.50 (3H, m), 6.83 (1H, s), 7.27 (2H, broad s), 9.65 (1H, d, J=8.0 Hz).

EXAMPLE 25

(1) 2-(2-Formamidothiazol-4-yl)-2-(2-tert-butoxycarbonylaminoethoxyimino)acetic acid (syn isomer, 2 g.) and 7-amino-3-(1,3,4-thiadiazol-2-yl)thiomethyl-3-cephem-4-carboxylic acid (1.8 g.) were treated in a similar manner to that of Example 20-(1) to give 7-[2-(2-formamidothiazol-4-yl)-2-(2-tert-butoxycarbonylaminoethoxyimino)acetamido]-3-(1,3,4-thiadiazol-2-yl)thiomethyl-3-cephem-4-carboxylic acid (syn isomer, 3.15 g.).

I.R. $\nu_{max}^{Nujol}$: 3400, 3200, 1780, 1680, 1540 cm$^{-1}$.

N.M.R. $\delta$(DMSO-d$_6$, ppm): 3.27 (2H, m), 3.68 (2H, m), 4.10 (2H, m), 4.43 (2H, q, J=13 Hz), 5.18 (1H, d, J=5 Hz), 5.85 (1H, d. d, J=8 Hz), 5 Hz), 7.40 (1H, s), 8.50 (1H, s), 9.53 (1H, s), 9.60 (1H, d, J=8 Hz), 12.82 (1H, broad s).

(2) 7-[2-Formamidothiazol-4-yl)-2-(2-tert-butoxycarbonylaminoethoxyimino)acetamido]-3-(1,3,4-thiadiazol-2-yl)thiomethyl-3-cephem-4-carboxylic acid (syn isomer, 3.0 g.) was treated with conc. hydrochloric acid (2.3 g.) in a similar manner to that of Example 23-(2) to give 7-[2-(2-aminothiazol-4-yl)-2-(2-aminoethoxyimino)acetamido]-3-(1,3,4-thiadiazol-2-yl)thiomethyl-3-cephem-4-carboxylic acid dihydrochloride (syn isomer, 2.5 g.).

I.R. $\nu_{max}^{Nujol}$: 3400-3100, 1770, 1710, 1650, 1625, 1570, 1540 cm$^{-1}$.

N.M.R. $\delta$(DMSO-d$_6$, ppm): 3.33 (2H, m), 3.77 (2H, broad s), 4.13-4.88 (4H, m), 5.22 (1H, d, J=5 Hz), 5.83 (1H, d, d, J=8 Hz, 5 Hz), 7.12 (1H, s), 10.03 (1H, d, J=8 Hz).

EXAMPLE 26

(1) 2-(2-Formamidothiazol-4-yl)-2-(2-tert-butoxycarbonylaminoethoxyimino)acetic acid (syn isomer, 2 g.) and 7-amino-3-(1-allyl-1H-tetrazol-5-yl)thiomethyl-3-cephem-4-carboxylic acid (2 g.) were treated in a similar manner to that of Example 20-(1) to give 7-[2-(2-formamidothiazol-4-yl)-2-(2-tert-butoxycarbonylaminoethoxyimino)acetamido]-3-(1-allyl-1H-tetrazol-5-yl)thiomethyl-3-cephem-4-carboxylic acid (syn isomer, 3.7 g.).

I.R. $\nu_{max}^{Nujol}$: 3400, 3250, 1780, 1680, 1540 cm$^{-1}$.

N.M.R. $\delta$(DMSO-d$_6$, ppm): 1.35 (9H, s), 3.32 (2H, m), 3.70 (2H, m), 4.10 (2H, m), 4.38 (2H, q, J=13 Hz), 4.67–5.50 (5H, m), 5.67–6.10 (2H, m), 7.45 (1H, s), 8.55 (1H, s), 9.60 (1H, d, J=8 Hz), 12.77 (1H, broad s).

(2) 7-[2-(2-Formamidothiazol-4-yl)-2-(2-tert-butoxycarbonylaminoethoxyimino)acetamido]-3-(1-allyl-1H-tetrazol-5-yl)thiomethyl-3-cephem-4-carboxylic acid (syn isomer, 3.5 g.) was treated with conc. hydrochloric acid (3.2 g.) in a similar manner to that of Example 23-(2) to give 7-[2-(2-aminothiazol-4-yl)-2-(2-aminoethoxyimino)acetamido]-3-(1-allyl-1H-tetrazol-5-yl)thiomethyl-3-cephem-4-carboxylic acid dihydrochloride (syn isomer, 3.0 g.).

I.R. $\nu_{max}^{Nujol}$: 3500–3100, 1770, 1700, 1670, 1625, 1560, 1540 cm$^{-1}$.

N.M.R. $\delta$(DMSO-d$_6$, ppm): 3.34 (2H, m), 3.7 (2H, broad s), 4.03–5.53 (4H, m), 5.58–6.55 (5H, m), 5.57–6.42 (2H, m), 7.10 (1H, s), 9.98 (1H, d, J=8 Hz).

EXAMPLE 27

(1) 7-Amino-3-(1,3,4-thiadiazol-2-yl)thiomethyl-3-cephem-4-carboxylic acid (1.8 g.) and 2-(2-formamidothiazol-4-yl)-2-(2-chloroethoxyimino)acetic acid (syn isomer, 1.4 g.) were treated in a similar manner to that of Example 24-(1) to give 7-[2-(2-formamidothiazol-4-yl)-2-(2-chloroethoxyimino)acetamido]-3-(1,3,4-thiadiazol-2-yl)thiomethyl-3-cephem-4-carboxylic acid (syn isomer, 2.18 g.).

I.R. $\nu_{max}^{Nujol}$: 1770, 1660 cm$^{-1}$.

N.M.R. $\delta$(DMSO-d$_6$, ppm): 3.38–4.06 (4H, m), 4.06–4.63 (4H, m), 5.15 (1H, d, J=5.0 Hz), 5.80 (1H, d, d, J=5.0 Hz, 8.0 Hz), 7.43 (1H, s), 8.47 (1H, s), 9.49 (1H, s), 9.63 (1H, d, J=8.0 Hz).

(2) 7-[2-(2-Formamidothiazol-4-yl)-2-(2-chloroethoxyimino)acetamido]-3-(1,3,4-thiadiazol-2-yl)thiomethyl-3-cephem-4-carboxylic acid (syn isomer, 2.0 g.) was treated with conc. hydrochloric acid (0.7 g.) in a similar manner to that of Example 24-(2) to give 7-[2-(2-aminothiazol-4-yl)-2-(2-chloroethoxyimino)acetamido]-3-(1,3,4-thiadiazol-2-yl)thiomethyl-3-cephem-4-carboxylic acid (syn isomer, 1.53 g.).

I.R. $\nu_{max}^{Nujol}$: 3300, 1770, 1670, 1630 cm$^{-1}$.

N.M.R. $\delta$(DMSO-d$_6$, ppm): 3.55–4.03 (4H, m), 4.06–4.78 (4H, m), 5.13 (1H, d, J=5.0 Hz), 5.75 (1H, d. d, J=5.0 Hz, 8.0 Hz), 6.74 (1H, s), 9.47 (1H, s), 9.50 (1H, d, J=8.0 Hz).

EXAMPLE 28

(1) 7-Amino-3-(1H-1,2,3-triazol-5-yl)thiomethyl-3-cephem-4-carboxylic acid (1.7 g.) and 2-(2-formamidothiazol-4-yl)-2-(2-tert-butoxycarbonylaminoethoxyimino)acetic acid (syn isomer, 2 g.) were treated in a similar manner to that of Example 20-(1) to give 7-[2-(2-formamidothiazol-4-yl)-2-(2-tert-butoxycarbonylaminoethoxyimino)acetamido]-3-(1H-1,2,3-triazol-5-yl)thiomethyl-3-cephem-4-carboxylic acid (syn isomer, 2.4 g.).

I.R. $\nu_{max}^{Nujol}$: 3200, 1780, 1690, 1550 cm$^{-1}$.

N.M.R. $\delta$(DMSO-d$_6$, ppm): 1.38 (9H, s), 3.32 (2H, m), 3.72 (2H, m), 4.12 (4H, m), 5.25 (1H, d, J=5 Hz), 5.88 (1H, d, d, J=8 Hz, 5 Hz), 7.52 (1H, s), 8.03 (1H, s), 8.57 (1H, s), 9.75 (1H, d, J=8 Hz), 12.92 (1H, m).

(2) 7-[2-(2-formamidothiazol-4-yl)-2-(2-tert-butoxycarbonylaminoethoxyimino)acetamido]-3-(1H-1,2,3-triazol-5-yl)thiomethyl-3-cephem-4-carboxylic acid (syn isomer, 2.1 g.) was treated with conc. hydrochloric acid (1.3 g.) in a similar manner to that of Example 21-(2) to give 7-[2-(2-aminothiazol-4-yl)-2-(aminoethoxyimino)acetamido]-3-(1H-1,2,3-triazol-5-yl)thiomethyl-3-cephem-4-carboxylic acid (syn isomer, 0.7 g.).

I.R. $\nu_{max}^{Nujol}$: 3300, 3150, 1760, 1660, 1610, 1570, 1530 cm$^{-1}$.

N.M.R. $\delta$(DMSO-d$_6$, ppm): 3.17 (2H, m), 3.52 (2H, m), 4.30 (4H, m), 5.02 (1H, d, J=5 Hz), 5.67 (1H, d, d, J=8 Hz, 5 Hz), 6.78 (1H, s), 7.75 (1H, s), 9.30 (1H, m).

EXAMPLE 29

(1) Vilsmeier reagent was prepared from N, N-dimethylformamide (0.98 g.) and phosphoryl chloride (2.05 g.) in ethyl acetate (6 ml.) in a usual manner. 2-[2-(tert-Butoxycarboxamido)ethyoxyimino]-2-(2-formamidothiazol-4-yl)acetic acid (syn isomer) (4.0 g.) was added to the stirred suspension of the Vilsmeier reagent in ethyl acetate (26 ml.) under ice cooling. The resulting mixture was added to a solution of 7-amino-3-(1,3,4-thiadiazol-2-yl)thiomethyl-3-cephem-4-carboxylic acid (3.7 g.) and trimethylsilylacetamide (8.7 g.) in tetrahydrofuran (37 ml.) at $-25°$ C. and the mixture was stirred for 30 minutes at $-15°$ C. After addition of water (100 ml.) and tetrahydrofuran (40 ml.) to the reaction mixture, the organic layer was separated. To the organic layer was added water (100 ml.) and then the mixture was adjusted to pH 7.5 with sodium bicarbonate. The aqueous layer was separated and thereto was added tetrahydrofuran. The mixture was adjusted to pH 3.0 with 10% hydrochlonic acid. The organic layer was separated, washed with a saturated aqueous solution of soduum chloride, dried over magnesium sulfate and evaporated under reduced pressure to give 7-[2-[2-(tert-butoxycarboxamido)ethoxyimino]-2-(2-formamidothiazol-4-yl)acetamido]-3-(1,3,4-thiadiazol-2-yl)-thiomethyl-3-cephem-4-carboxylic acid (syn isomer) (5.9 g.).

I.R. $\nu$(Nujol) 3400–3100, 1780, 1680, 1540 cm$^{-1}$.

N.M.R. (DMSO-d$_6$, ppm) 1.35 (9H, s), 2.95–3.53 (2H, m), 3.53–3.90 (2H, m), 3.90–4.28 (2H, m), 4.45 (2H, q, J=14 Hz), 5.17 (1H, d, J=5 Hz), 5.85 (1H, dd, J=5 and 8 Hz), 7.4 (1H, s), 8.52 (1H, s), 9.53 (1H, s), 9.57 (1H, d, J=8 Hz), 12.6 (1H, broad s).

(2) A mixture of 7-[2-[2-(tert-butoxycarboxamido)ethoxyimino]-2-(2-formamidothiazol-4-yl)acetamido]-3-(1,3,4-thiadiazol-2-yl)thiomethyl-3-cephem-4-carboxylic acid (syn isomer) (5.8 g.) and formic acid (60 ml.) was stirred for 3 hours at 40° C. The reaction mixture was evaporated under reduced pressure. The residue was pulverized in acetonitrile and then washed with diethyl ether to give 7-[2-(2-aminoethoxyimino)-2-(2-formamidothiazol-4-yl)acetamido]-3-(1,3,4-thiadiazol-2-yl)thiomethyl-3-cephem-4-carboxylic acid formate (syn isomer) (4.4 g.).

N.M.R. (DMSO-d$_6$, $\delta$, ppm) 3.23 (2H, m), 4.07–4.77 (4H, m), 5.08 (1H, d, J=5 Hz), 5.78 (1H, dd, J=5 and 8 Hz), 7.52 (1H, s), 8.53 (1H, s), 9.5 (1H, s), 9.55 (1H, d, J=8 Hz), 3.52 (2H, m).

EXAMPLE 30

To a solution of 7-[2-(2-aminothiazol-4-yl)-2-(2,2,2-trifluoroethoxyimino)acetamido]cephalosporanic acid (syn isomer, 2.6 g.) in phophate buffer solution (pH 6.4) was added 1,3,4-thiadiazol-2-ylthiol (0.9 g.), and stirred at 60° to 65° C. for 4 hours, while adjusting to pH 6.4 to 6.5 with a saturated aqueous solution of sodium bicarbonate. The solution was adjusted to pH 3.2 with 10% hydrochloric acid, and then the precipitates were collected by filtration and dried to give 7-[2-(2-aminothiazol-4-yl)-2-(2,2,2-trifluoroethoxyimino)acetamido]-3-(1,3,4-thiadiazol-2-ylthiomethyl)-3-cephem-4-carboxylic acid (syn isomer).

I.R. $\nu_{max}^{Nujol}$: 3400-3200, 1780, 1680, 1630, 1530 cm$^{-1}$.

N.M.R. $\delta$(DMSO-d$_6$, ppm): 3.71 (2H, q, J=17 Hz), 4.46 (2H, q, J=13 Hz), 4.72 (2H, q, J=8 Hz, 5 Hz), 5.18 (1H, d, J=5 Hz), 5.80 (1H, dd, J=5 Hz, 8 Hz), 6.88 (1H, s), 9.81 (1H, d, J=8 Hz), 9.58 (1H, s).

What we claim is:

1. A compound of the formula:

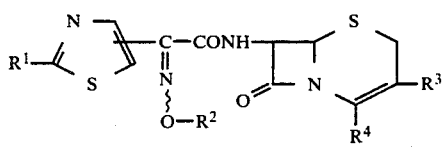

wherein
R$^1$ is amino or protected amino,
R$^2$ is lower alkyl substituted with 1 to 3 halogen atoms,
R$^3$ is thiadiazolylthiomethyl which may be substituted with lower alkyl, or tetrazolylthiomethyl which may be substituted with lower alkyl or lower alkenyl, and
R$^4$ is carboxy or protected carboxy,
and a pharmaceutically acceptable salt thereof.

2. A compound of the claim 1, which is syn isomer.

3. A compound of claim 1, wherein R$^2$ is lower alkyl substituted with 1 to 3 fluorine atoms.

4. A compound of claim 2, wherein
R$^1$ is amino or lower alkanoylamino,
R$^3$ is thiadiazolylthiomethyl which may be substituted with lower alkyl, or tetrazolylthiomethyl which may be substituted with lower alkyl or lower alkenyl, and
R$^4$ is carboxy or esterafied carboxy.

5. A compound of the claim 4, wherein
R$^1$ is amino or lower alkanoylamino,
R$^3$ is thiadiazolylthiomethyl, or tetrazolylthiomethyl which may be substituted with lower alkyl or lower alkenyl, and
R$^4$ is carboxy.

6. A compound of the claim 5, which is 7-[2-(2-aminothiazol-4-yl)-2-(2-chloroethoxyimino)acetamido]-3-(1-allyl-1H-tetrazol-5-ylthiomethyl)-3-cephem-4-carboxylic acid (syn isomer).

7. A compound of the claim 5, which is 7-[2-(2-aminothiazol-4-yl)-2-(2-chloroethoxyimino)acetamido]-3-(1,3,4-thiadiazol-2-ylthiomethyl)-3-cephem-4-carboxylic acid (syn isomer).

8. A compound of the claim 5, which is 7-[2-(2-aminothiazol-4-yl)-2-(2-bromoethoxyimino)acetamido]-3-(1,3,4-thiadiazol-2-ylthiomethyl)-3-cephem-4-carboxylic acid (syn isomer).

9. A compound of the claim 5, which is 7-[2-(2-aminothiazol-4-yl)-2-(2,2,2-trifluoroethoxyimino)acetamido]-3-(1-methyl-1H-tetrazol-5-ylthiomethyl)-3-cephem-4-carboxylic acid (syn isomer).

10. A compound of the claim 5, which is 7-[2-(2-aminothiazol-4-yl)-2-(2,2,2-trifluoroethoxyimino)acetamido]-3-(1-allyl-1H-tetrazol-5-ylthiomethyl)-3-cephem-4-carboxylic acid (syn isomer).

11. A compound of the claim 5, which is 7-[2-(2-aminothiazol-4-yl)-2-(2,2,2-trifluoroethoxyimino)acetamido]-3-(1,3,4-thiadiazol-2-ylthiomethyl)-3-cephem-4-carboxylic acid (syn isomer).

12. A pharmaceutical antimicrofial composition which comprises an effective amount of a compound of claim 1 in association with a pharmaceutically acceptable, substantially non-toxic carrier or excipient.

* * * * *